(12) United States Patent
Ladisch et al.

(10) Patent No.: US 10,144,785 B2
(45) Date of Patent: Dec. 4, 2018

(54) LIQUEFACTION BIOMASS PROCESSING WITH HEAT RECOVERY

(75) Inventors: Michael R. Ladisch, West Lafayette, IN (US); Nathan Mosier, West Lafayette, IN (US); Youngmi Kim, Woodbury, MN (US); Justin van Rooyen, Boston, MA (US)

(73) Assignee: Purdue Research Foundation, West Lafayette ( * ) Notice: Subject to any disclaimer, the term of this patent is extended or adjusted under 35 U.S.C. 154(b) by 50 days.

(21) Appl. No.: 13/754,412

(22) PCT Filed: Jul. 29, 2011

(86) PCT No.: PCT/US2011/045958
§ 371 (c)(1),
(2), (4) Date: Aug. 28, 2013

(87) PCT Pub. No.: WO2012/016180
PCT Pub. Date: Feb. 2, 2012

(65) Prior Publication Data
US 2013/0330782 A1 Dec. 12, 2013

Related U.S. Application Data

(60) Provisional application No. 61/369,445, filed on Jul. 30, 2010.

(51) Int. Cl.
| | |
|---|---|
| C08B 1/00 | (2006.01) |
| C12N 1/22 | (2006.01) |
| C12P 7/10 | (2006.01) |
| C12P 19/02 | (2006.01) |
| C12P 19/14 | (2006.01) |

(52) U.S. Cl.
CPC .............. *C08B 1/00* (2013.01); *C12N 1/22* (2013.01); *C12P 7/10* (2013.01); *C12P 19/02* (2013.01); *C12P 19/14* (2013.01); *Y02E 50/16* (2013.01); *Y02E 50/17* (2013.01); *Y02P 20/124* (2015.11); *Y02P 20/59* (2015.11)

(58) Field of Classification Search
None
See application file for complete search history.

(56) References Cited

U.S. PATENT DOCUMENTS

| | | | | |
|---|---|---|---|---|
| 4,200,734 A | * | 4/1980 | Muehlenbrock et al. | 528/503 |
| 5,411,594 A | * | 5/1995 | Brelsford | B01J 19/242 127/1 |
| 5,536,325 A | * | 7/1996 | Brink | B02C 13/18 127/37 |
| 2009/0035826 A1 | * | 2/2009 | Tolan | B01D 3/001 435/99 |
| 2009/0240088 A1 | * | 9/2009 | Fenton | B01F 3/1214 568/840 |
| 2010/0203605 A1 | * | 8/2010 | Kim et al. | 435/161 |

FOREIGN PATENT DOCUMENTS

WO    WO 2009/158621    * 12/2009    ............. D21C 11/00

OTHER PUBLICATIONS

Alfa Laval brochure, retrieved from the Internet: Alfa Laval Thermal Heat Exchanger Facts, vol. 7, 1997, pp. 1-4 http://canaley.com/wp-content/uploads/2012/01/FACTS-7.pdf.*
Mosier et al., Biotechnol. Prog. 2001, vol. 17, pp. 474-480.*
Ehrhardt et al., Rheology of Dilute Acid Hydrolyzed Corn Stover at High Solids Concentration, Appl. Biochem Biotechnol, Feb. 2010;160(4):1102-15, published online: Mar. 31, 2009.*

* cited by examiner

*Primary Examiner* — Thomas J. Visone
*Assistant Examiner* — Evelyn Y Pyla
(74) *Attorney, Agent, or Firm* — Woodard, Emhardt, Moriarty, McNett & Henry, LLP

(57) ABSTRACT

Described are processes that include the non-enzymatic, hydrolytic liquefaction of lignocellulosic biomass to form digest slurries and heat recovery from such digest slurries. Due to enhanced flow properties of the digest slurries such heat recovery can be efficiently conducted in spiral, plate and frame or other heat exchanger designs, with the recovered heat going to unit operations of the process such as heating incoming pretreatment media for the liquefaction. Processes can also involve additional hydrolytic digestion of some or all of the initial slurry components with enzyme and/or additional heat recovery from the initial slurry by direct contact heat exchange in which a portion of the digest slurry liquids is flashed to vapor and that vapor is condensed onto incoming lignocellulosic biomass to the process. Processes as described can be integrated into ethanol manufacture by fermentation of sugars from the digested compositions.

34 Claims, 22 Drawing Sheets

Schematic representation of enzyme mimetic liquefied in using heat exchanger to recover thermal energy.

Schematic representation of combined steam pretreatment and enzyme mimetic liquefaction using combined spiral heat exchange with auxiliary heat recovery from a biomass heat source.

Untreated 15%Solids Mixed Hardwood

LIQUEFACTION BIOMASS PROCESSING WITH HEAT RECOVERY

This application is a continuation of International Application Serial No. PCT/2011/045958, filed Jul. 29, 2011, which claims the benefit of U.S. Provisional Application Ser. No. 61/369,445 filed Jul. 30, 2010, each of which is hereby incorporated by reference in its entirety.

BACKGROUND

The present invention relates generally to the utilization of lignocellulosic biomass, and in certain embodiments to processes that involve processing biomass that has been subject to liquefaction to recover heat therefrom, and the integration of such processing into the manufacture of useful products such as ethanol.

As further background, in the conversion of biomass to products of commerce, it is desired that the costs and equipment associated with the physical and chemical treatments of the biomass be minimized. Downstream products of biomass are often commoditized from other sources, and thus biomass-based manufacturing costs must be held tightly in check.

One challenge that is presented in biomass processing is the difficulty in moving the biomass to, within and through equipment needed to physically and/or chemically treat the biomass. Processing at low biomass solids content enhances flowability and transport in some cases, but minimizes productivity for the downstream product, often fatal to the commercial viability of the process. Processing at high biomass solids enhances productivity, but the attendant thick, wet mass is difficult to move, consumes high levels of energy for transport, and/or cannot effectively be processed through heat recovery equipment such as heat exchangers due to an in ability to pump the mixture and/or plugging of the heat exchangers. The effective recovery and recycle of energy used in processing of the biomass can also be vital to commercial viability.

In one field of interest, fuel ethanol has been produced by fermentation of biomass feedstocks derived from plants. Currently, fuel ethanol is commercially produced from feedstocks of cornstarch, sugar cane and sugar beets. These materials, however, find significant competing uses in the food industry, and their expanded use to make fuel ethanol is met with increased prices and disruption of other industries. Alternative fermentation feedstocks and technologies for their utilization are thus highly sought after.

Lignocellulosic biomass feedstocks are available in large quantities and are relatively inexpensive. Such feedstocks are available in the form of agricultural wastes such as corn stover, corn fiber, wheat straw, barley straw, oat straw, oat hulls, canola straw, soybean stover, grasses such as switch grass, miscanthus, cord grass, and reed canary grass, forestry wastes such as wood, e.g. aspen wood and sawdust, and sugar processing residues such as bagasse and beet pulp. Cellulose from these feedstocks is converted to sugars, which are then fermented to produce the ethanol.

A difficulty in using lignocellulosic feedstocks is that the useful sugar content of the biomass is largely caught up in natural polymers such as cellulose and hemicellulose, and conditions or agents must be used to convert those polymeric substances to simple sugars. For this reason, research has focused upon methods for processing lignocellulosic biomass to create process feeds containing simple sugars. For such methods to succeed, high starting biomass solids levels and effective digestion of the biomass are important to providing a fermentable medium with high enough sugar levels to make for viable fermentations. However, such high solids levels present many difficulties in manufacturing, as discussed above.

Despite previous efforts relating to processing lignocellulosic biomass feedstocks and their ultimate use in the production of ethanol and other products, needs remain for improved and alternative biomass utilization processes, including in the production of ethanol or other useful substances from fermentation. In certain of its aspects, the present invention is addressed to these needs.

SUMMARY

In one aspect, processes for the liquefaction of lignocellulosic biomass are provided which result in a flowable biomass digest slurry having rheological properties enabling its effective passage through heat exchangers for heat recovery. Such processes can be non-enzymatic (e.g. through acid-catalyzed hydrolysis), and can be utilized in the production of ethanol from biomass. Accordingly, in one embodiment, provided is a method for manufacturing ethanol from a particulate lignocellulosic biomass feedstock. The method includes subjecting a first amount of particulate lignocellulosic biomass feedstock to hydrolytic liquefaction under heated conditions to form a hot liquefied digest slurry comprising (i) dissolved biomass components representing at least 10% by weight on a dry weight basis of the biomass feedstock and comprising at least xylose, and (ii) undissolved lignocellulosic biomass particulates comprising lignin and cellulose. The hot liquefied digest slurry is cooled by pumping the slurry through a first passage of a heat exchanger so as to transfer heat to a cooler liquid in a second passage of the heat exchanger. After the cooling of the slurry, the xylose is fermented (as then present, or after additional sugar formation from the biomass) to form ethanol. In one mode of operation, the process also includes the step of contacting the liquified digest slurry with a cellulolytic enzyme so as to hydrolyze amounts of the cellulose in the particulates to form glucose, and potentially also to form additional xylose relative to that present in the original liquefied digest slurry. The xylose and glucose can then be fermented, alone or together, to form ethanol.

In another embodiment, the invention provides a method for processing lignocellulosic biomass, comprising that includes incubating a mixture including a first amount of a solid, particulate lignocellulosic biomass and a first amount of a liquid processing medium containing at least one dicarboxylic acid under heated conditions effective to form a biomass digest composition exhibiting a lower yield stress than the mixture and in which at least 10% by weight of the solid, particulate biomass has been converted to dissolved biomass components in the liquid medium, the digest composition also including undissolved lignocellulosic biomass particulates. A flowable liquid digest medium at least partially comprised of such dissolved biomass components and undissolved lignocellulosic biomass particulate is passed through a first passage of a heat exchanger while a second amount of a liquid processing medium containing at least one dicarboxylic acid is passed through a second passage of the heat exchanger so as to transfer heat from said flowable liquid digest medium to said second amount of liquid processing medium to provide a preheated liquid processing medium. The preheated liquid processing medium is combined with a second amount of solid, particulate biomass.

Another embodiment provides a method for recovering heat from pretreated lignocellulosic biomass. The method involves pumping a hot aqueous liquid digest slurry comprising dissolved biomass solids and undissolved lignocellulosic biomass particulates through a first passage of a heat exchanger at a linear velocity sufficiently high to cause the particulates to enhance the generation of turbulent flow. The digest slurry is characterized by having at least 15% by weight total biomass solids on a dry weight basis, where 10% to 45% of the total biomass solids are dissolved in the aqueous liquid, and where the undissolved biomass particulates comprise lignin and cellulose. The method also includes recovering heat from the hot aqueous liquid digest slurry by transferring heat from the slurry to a fluid pumped through a second passage of the heat exchanger. Such fluid can, for example, be a processing medium to be contacted with additional biomass feedstock in the creation of additional amounts of the hot aqueous liquid digest slurry.

Additional embodiments as well as features and advantages of the inventive embodiments will be apparent from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated embodiments, and such further applications of the principles of the invention as described herein being contemplated as would normally occur to one skilled in the art to which the invention relates.

Figure 1:
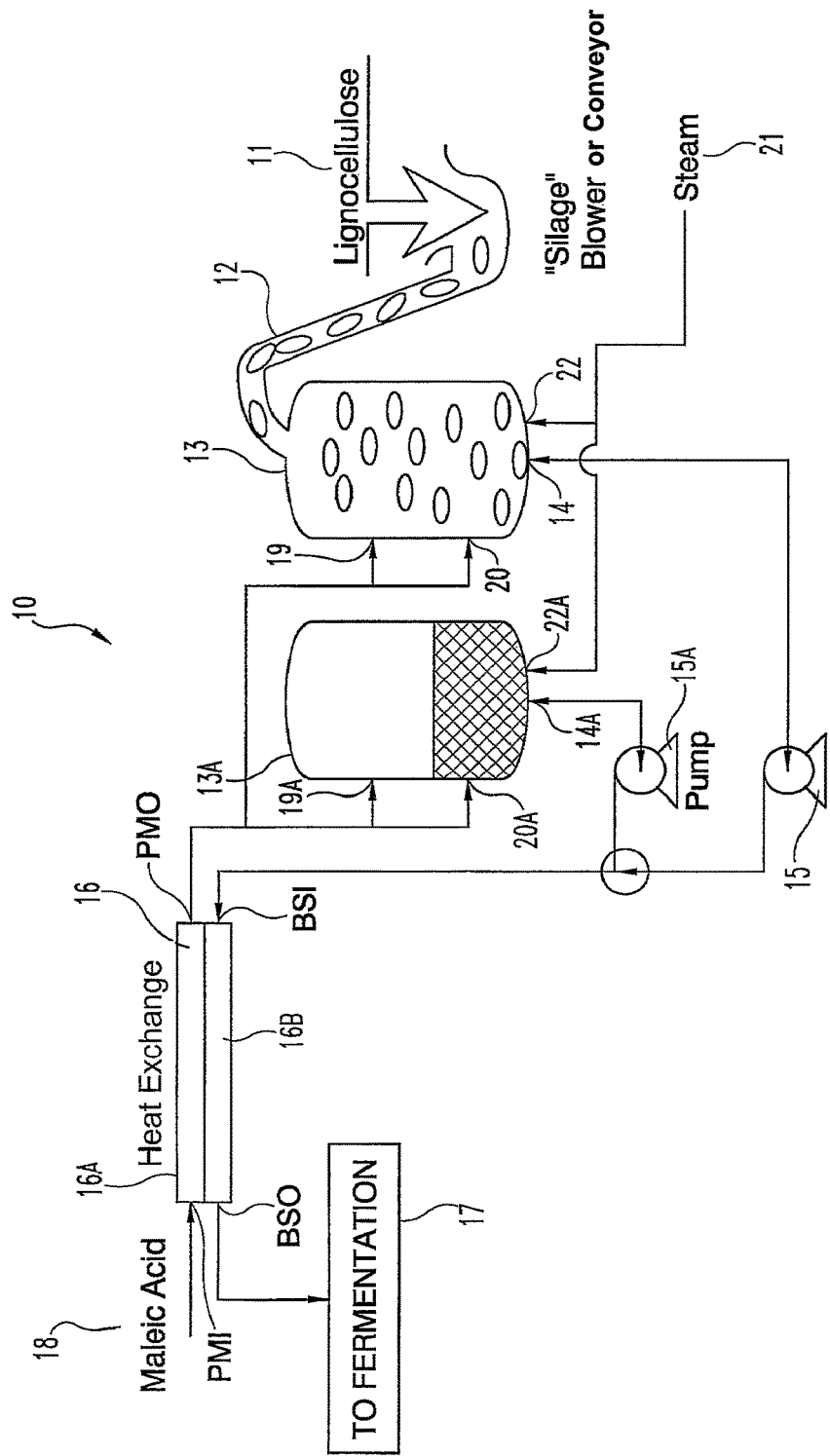
FIG. 1 is a schematic diagram of processing steps in one embodiment of a bioethanol production process of the invention.

As disclosed above, certain aspects of the present invention relate to methods for processing lignocellulosic biomass under liquefaction conditions to result in a flowable biomass digest slurry that can be effectively passed through manufacturing equipment needed for downstream processing, including in some embodiments heat exchangers used to recover and recycle heat introduced to the system. With reference to FIG. 1, shown is one embodiment of a system and method of biomass liquefaction and processing with heat recovery. System 10 includes a source 11 of lignocellulosic biomass. A biomass transfer device 12 such as a blower (e.g. a silage blower or similar apparatus), conveyor or other mechanism, transfers amounts of biomass 11 into pretreatment vessel 13. Vessel 13 has an outlet 14 fluidly connected to a pump 15, such as a centrifugal pump. Pump 15 is situated and effective to pump materials to heat exchanger 16, and in particular to a first passage 16B of heat exchanger 16, isolated from a second passage 16A thereof. Passage 16B has a biomass slurry inlet "BSI" and an outlet "BSO" for receiving and expelling a biomass digest slurry, respectively. Outlet BSO leads to downstream system components, which can include a vessel 17 for fermentation, and/or other units. System 10 also includes a source 18 of a chemical pretreatment medium and in particular embodiments an aqueous solution of a dicarboxylic acid, as discussed herein. Source 18 is fluidly coupled to passage 16A of heat exchanger 16. Heat exchanger 16 can be of any suitable variety, but is preferably a spiral heat exchanger or a plate and frame heat exchanger. In this regard, the flowable digest slurry generated by liquefaction processing can be effectively pumped by pump 15, and can be passed through spiral, plate and frame, or other heat exchangers having narrow gap widths (e.g. about 1 cm to about 4 cm, in some cases about 1 cm to about 2 cm) while avoiding plugging. In certain embodiments, the digest slurry can be passed through the heat exchanger undiluted, while in others the slurry can be diluted with a minor amount of water if needed to enhance flow. Still further, in beneficial processes, even while passing through such narrow gap heat exchangers, the digest slurry has rheologic properties enabling a pressure drop of no greater than about 20 pounds per square inch (psi) between the inlet BSI and outlet BSO while the slurry is being pumped at a liquid pressure not exceeding about 100 psi through passage 16B. The aqueous lignocellulosic biomass can be passed through the heat exchanger(s) of the system at any suitable flow rate. Flow rates of the slurry through the heat exchanger during such conditions can be at least about 20 gallons (US) per minute (gal/min) and will typically be in the range of about 200 to about 1000 gal/min, and/or with linear velocities of at least about 1 foot/second and typically in the range of about 10 to about 50 feet/second. "Linear velocity" as used in this context means the average distance a particle in the fluid travels per unit of time. These flow rates and linear velocities can be achieved in certain embodiments in heat tube-in-shell exchangers having 20 to 500 tubes for carrying the slurry. The ability to achieve relatively high flow rates at reasonable pump pressures is facilitated by the liquefaction processing, which also leaves residual biomass particles in the digest slurry that enhance the generation of turbulent flow under these conditions. The enhanced turbulent flow can be beneficial, for example, in increasing the efficiency of heat transfer in heat exchangers as described herein. Such heat exchangers can thereby also be designed to have reduced presence of stubs (e.g. as occur between plates in spiral heat exchangers), baffles or other physical barriers in the flow gaps which are designed to generate turbulence. Such reductions in physical barriers can in turn reduce risks of plugging of the heat exchanger with the biomass slurry. The heat exchangers with relatively sparse populations of stubs or other barriers can have sufficient spaces between the stubs/barriers to enable the particles of the digest slurry to pass while creating regions of flow disturbance downstream from the passageway formed by the space between the stubs/barriers. At the same time the stubs/barriers can position the adjacent surfaces of the heat exchanger to a desired distance of 1 to 10 cm between adjacent surfaces, thereby providing a large heat transfer area per unit volume of the heat exchanger. In certain embodiments, the stubs or other barriers are located at a spacing of 5 cm to 25 cm from one another in a such a manner that the channels formed between the stubs are 50 to 500 times larger than the average particle size of biomass particles in the liquefied digest slurry, where average (wet particle) size can range between 50 and 500 microns.

Passage 16A of heat exchanger 16 has a pretreatment medium inlet (PMI) and a pretreatment medium outlet (PMO). Outlet PMO is fluidly coupled to a first inlet 19 and a second inlet 20 to vessel 13 for delivery of the pretreatment medium into vessel 13. Inlet 19 is positioned in an upper region of vessel 13 above an anticipated fill level for a mixture of the pretreatment medium and the lignocellulosic biomass 11. Inlet 20 is positioned on vessel 13 at a level anticipated to be below a fill level of such mixture. In this fashion, pretreatment medium can be added to head space within the vessel 13 and directly to the mixture in vessel 13 as desired, and with appropriate valving can be selectively added in either of these two regions.

System 10 as shown also includes a second pretreatment vessel 13A equipped correspondingly to vessel 13. In this fashion semi-batch processes are enabled in which a first batch of lignocellulosic biomass can be incubated under heated conditions for the pretreatment to create a digest slurry while a second batch of lignocellulosic biomass is loaded and prepared for a similar treatment. Vessel 13A is thus equipped with a biomass slurry outlet 14A fluidly coupled to a pump 15A which is in turn fluidly coupled to biomass slurry inlet (BSI) of heat exchanger passage 16B. Alternate flows from pump 15 and 15A can be selectively provided to heat exchanger 16 with appropriate valving, as those skilled in the art will understand. Similarly, vessel 13A includes a first pretreatment medium 19A in the anticipated head space of vessel 13A, and a second pretreatment inlet opening 20A, below the anticipated fill line vessel 13A.

A source of steam 21 is coupled to both vessels 13 and 13A, desirably valved to alternately feed steam to vessels 13 and 13A at selected times. Thus, steam source 21 feeds into steam inlet 22 of vessel 13, and into steam inlet 22A of vessel 13A and is valved for selective feed to inlets 22 and 22A.

In use for pretreatment, system 10 can be operated as follows. Lignocellulosic biomass 11 is fed by device 12 into vessel 13. A preconditioning medium is passed from source 18 through passage 16A of heat exchanger 16 and into vessel 13 via inlets 19 and/or 20. The pretreatment medium combines with the biomass to form a mixture. With the aid of direct injected steam from source 21, the biomass in vessel 13 is treated at temperatures as described herein (e.g. between about 100 and 200 degrees C.) under hydrolytic liquefaction conditions to form a biomass digest slurry. This biomass digest slurry is pumped from outlet 14 using pump 15 and passed through passage 16B of heat exchanger 16. As it passes through passage 16B, the biomass slurry transfers heat to incoming pretreatment medium from source 18 simultaneously passing through passage 16A. This incoming pretreatment medium is thereby heated for use to treat a subsequent batch of lignocellulosic biomass 11, which those skilled in the art will understand could be in the same vessel or in a different vessel cycled in the system. The cooled biomass slurry exiting passage 16B via biomass slurry outlet (BSO) is then processed further for product formation therefrom, for example through fermentation processing as described herein. It will be understood that a number of additional steps or conditions can be applied to the biomass slurry prior to fermentation or final product formation, including for example neutralization, additional heat exchanger operations, additional hydrolytic pretreatments (e.g. with cellulosic enzymes as described hereinbelow), or other operations useful to the manufacture of the target biomass-derived commercial product.

In the particular system 10 shown, at the processing stage shown, vessel 13A contains a liquid biomass slurry (LBS) from a prior-conducted liquefaction pretreatment. It is this slurry LBS that would be pumped by via pump 15A through passage 16B of heat exchanger 16, as the incoming pretreatment medium from source 18 is being routed to vessel 13 for processing of the biomass batch as discussed above. Such a system having two pretreatment vessels can, as discussed above, be used to effect a semi-batch operation in which consecutive batches are processed, with at least part of the processing of the two batches occurring simultaneously. Furthermore, additional vessels for pretreatment could be added to the system as needed to optimize such a semi-batch process, e.g. creating a three-vessel, or four-vessel initial liquefaction unit. The number of such pretreatment vessels will depend upon various parameters including for example the pretreatment hold times utilized, the speed with which new batches of biomass 11 and pretreatment medium can be prepared, space considerations, and others.

Figure 2:
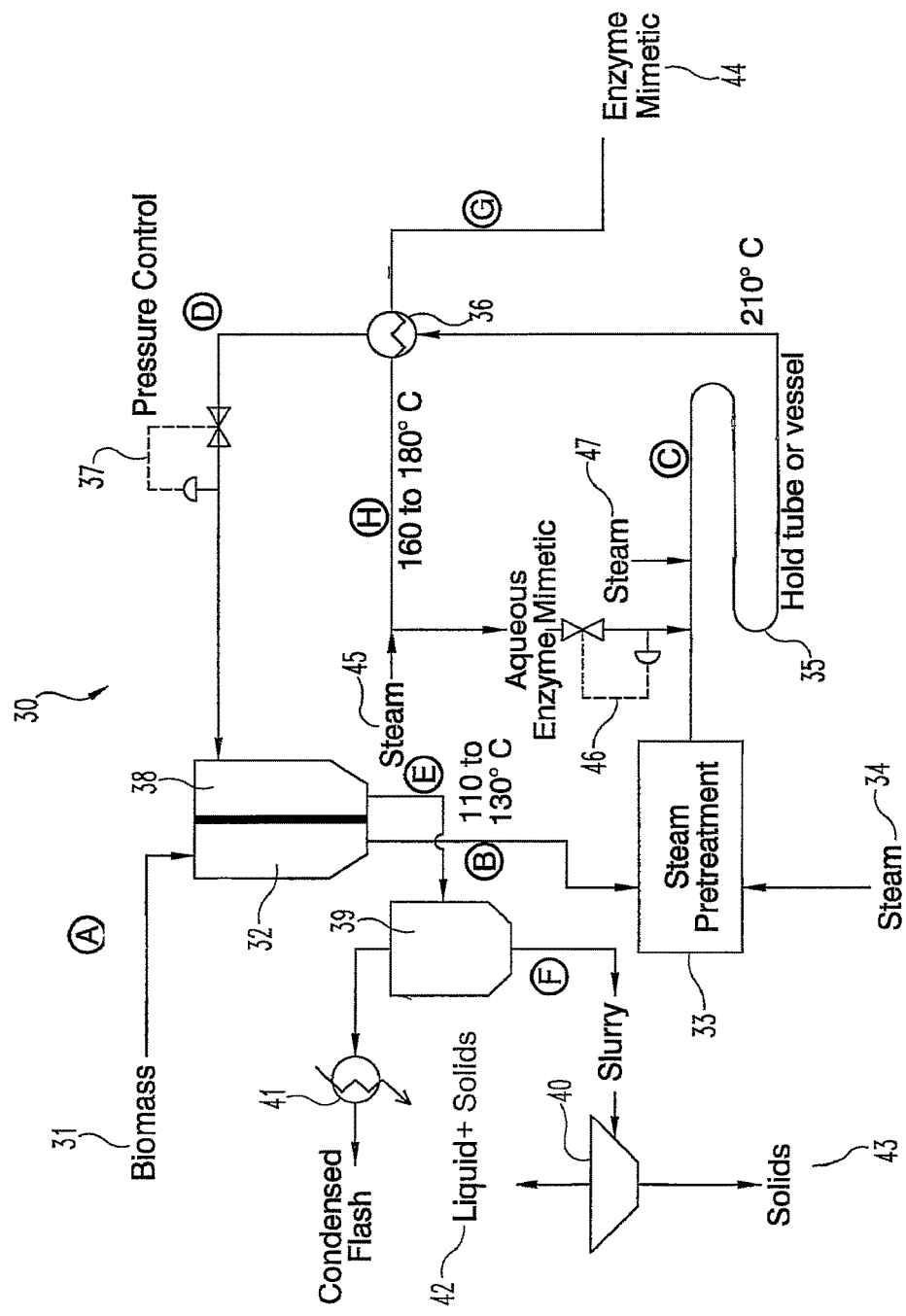
FIG. 2 is a schematic diagram of processing steps in another embodiment of a bioethanol production process of the invention.

With reference now to FIG. 2, shown is another system 30 for biomass processing that includes biomass liquefaction and heat recovery operations. System 30 includes the source of lignocellulosic biomass 31 transferable to a direct contact heat exchange unit 32. Biomass 31 can be transferred from unit 32 to a steam pretreatment vessel 33, wherein the biomass can be treated with steam from steam source 34. Steam treated biomass from vessel 33 is transferred to a holding zone which can for example be a hold coil designed to provided a given residence time under flow conditions, or a hold vessel in which the material is collected and incubated in combination with a pretreatment medium. After an appropriate hold period for pretreatment, a biomass digest slurry with liquid biomass and particulate is passed through heat exchanger 36, desirably a spiral heat exchanger, in which it transfers heat to incoming pretreatment medium. The thus-cooled biomass digest slurry passes through and beyond a pressure controller 37 such as a pressure control valve which controls pressure upstream of the controller 37, at which point the pressure applied to the material is reduced and the material enters a flash cooler 38. A portion of the biomass slurry is flashed to vapors in flash cooler 38. These vapors enter direct contact heat exchanger 32 and condense upon and thereby heat incoming biomass 31. For additional information about the design, components and use of such direct contact heat exchangers for energy recovery and incoming biomass heating, reference can be made to U.S. Pat. No. 7,566,383, which is hereby incorporated herein by reference in its entirety. The non-vaporized portion of the biomass slurry exits the flash cooler 38 and passes to a flash chamber or flash drum 39. Additional vapors are flashed from the biomass slurry, cooling it further, desirably to a temperature appropriate for processing in centrifuge 40. Flashed vapors from chamber 39 are condensed in heat exchanger 41 and sent to recycle or waste in accordance with system design. Desirably, the biomass slurry entering centrifuge 40 is at a temperature of less than 100° C. Centrifuge 40 is used to separate the biomass slurry into a liquid fraction 42, for example containing about 3 to about 10 percent dissolved solids, and a solids-rich fraction 43, for example containing about 25 to 35 percent by weight solids overall. The liquid fraction 42 in certain embodiments is rich in monomeric xylose which can be fermented to ethanol as described herein. The solids-rich fraction 43 contains high levels of undissolved biomass particulate containing lignin and cellulose. In certain aspects, this stream 43 can be hydrolyzed with a cellulolytic enzyme as described herein to form monomeric glucose in solution, which can be fermented ethanol.

System 30 can be operated to control heat applied to the system, and to recover and recycle previously-applied heat. At various process stages, the biomass and pretreatment medium will have varying temperatures. These temperatures may be selected from among temperatures suitable to achieve digestion of the biomass as described herein. In certain embodiments, the lignocellulosic biomass feedstock at stage "A" in the system, that being the initial feed prior to applying any system heat to the biomass, will be at about ambient temperatures, for example in the range of about 20° C. to 30° C. At stage "B", after the biomass has been subjected to direct contact heat exchange in exchanger zone 32 using vapors flashed in chamber 38, the biomass will have a significantly higher temperature than at stage "A", for example in some forms about 100° C. to about 140° C. At stage "C" of system 30, after steam injection and combination with hot pretreatment medium, and during hydrolytic liquefaction pretreatment preferably with a dicarboxylic acid medium, the biomass slurry will have a temperature greater than that of the biomass at stage "B", for example in the range of about 120° C. to about 210° C. At stage "D", after the hydrolytic liquefaction to form a digest slurry and passage through heat exchanger 36, the digest slurry will have a temperature lower than that at stage "C", for example in the range of about 110° C. to about 160° C. At stage "E", after flash cooling in chamber 38, the digest slurry will have a temperature lower than that at stage "D", in certain modes in the range of about 100° C. to about 140° C.; and, at stage "F", after flash cooling in chamber 39, the digest slurry will have a temperature lower than that at stage "E", for example in the range of about 70° C. to about 100° C.

On the pretreatment medium side, the pretreatment medium 44 at system feed stage "G" prior to heat exchanger 36, will have a temperature lower than that of the biomass digest slurry entering heat exchanger 36, for example in the range of about 20° C. to about 90° C. The pretreatment medium will be heated within exchanger 36 and at stage "H" will have a temperature greater than that at stage "G", for example in the range of about 120° C. to about 180° C. Steam 45, when used, will further heat the pretreatment medium prior to its combination with the biomass for liquefaction pretreatment within zone 35 as discussed above, to example providing a medium temperature of about 150° C. to about 200° C. at stage "I" of system 30. The pretreatment medium thereafter passes through pressure control device 46 and enters the liquefaction zone which, extending at least to pressure control device 37, is desirably operated at a pressure greater than the saturation vapor pressure of the pretreatment medium at the selected processing temperatures.

It will be understood that while systems 10 and 30 of FIGS. 1 and 2 disclose certain embodiments of the invention, other systems which capitalize upon the flowable nature of the product of the biomass liquefaction can also be implemented, and are contemplated as part of inventive embodiments disclosed herein.

Discussions will now turn to specific materials and conditions that can be used in systems 10 and 30, or other systems for liquefaction biomass processing with heat recovery. It will be understood to those skilled in the field that additional specific embodiments of the invention are contemplated where each of the specific materials or conditions as described below, or their combinations, are added to and/or substituted for materials or conditions discussed above for systems 10 and 30. In addition, certain discussions below relate to compositional analyses of digest slurry products that can be obtained through liquefaction processing. Operations of systems 10 and 30 to achieve, transfer and process such defined compositions are also considered specific embodiments of the invention.

The term "lignocellulosic biomass" as used herein is meant to refer to any type of biomass comprising lignin and cellulose such as, but not limited to, non-woody plant biomass, agricultural wastes and forestry residues and sugar-processing residues. For example, the lignocellulosic feedstock can include, but is not limited to, grasses, such as switch grass, cord grass, rye grass, miscanthus, mixed prairie grasses, or a combination thereof; sugar-processing residues such as, but not limited to, sugar cane bagasse and sugar beet pulp; agricultural wastes such as, but not limited to, soybean stover, corn fiber from grain processing, corn stover, oat straw, rice straw, rice hulls, barley straw, corn cobs, wheat straw, canola straw, oat hulls, and corn fiber; and forestry wastes, such as wood, including but not limited to, recycled wood pulp fiber, sawdust, hardwood, softwood, or any combination thereof. Further, the lignocellulosic biomass may comprise lignocellulosic waste or forestry waste materials such as, but not limited to, paper sludge, newsprint, cardboard and the like. Lignocellulosic biomass may comprise one species of fiber or, alternatively, a lignocellulosic biomass feedstock may comprise a mixture of fibers that originate from different lignocellulosic materials.

Typically, the lignocellulosic material will comprise cellulose in an amount greater than about 2%, 5% or 10% and preferably greater than about 20% (w/w) to produce a significant amount of glucose. The lignocellulosic material can be of higher cellulose content, for example at least about 30% (w/w), 35% (w/w), 40% (w/w) or more. Therefore, the lignocellulosic material may comprise from about 2% to about 90% (w/w), or from about 20% to about 80% (w/w) cellulose, or from 25% to about 70% (w/w) cellulose, or about 35% to about 70% (w/w) cellulose, or more, or any amount therebetween.

Prior to processing with chemical or biological agents, the lignocellulosic biomass can be mechanically processed to increase its surface area. Such mechanical processing may include, for example, reducing the biomass to a particulate by grinding, milling, agitation, shredding, or other types of mechanical action. The particulate biomass feedstock can have a particle size distribution providing an average, maximum particle dimension of at least about 1 mm in certain embodiments, and in typical embodiments at least about 3 mm. In some forms, the average, maximum particle dimension of the particulate biomass feedstock can be within the range of about 1 mm to about 20 mm, more particularly about 3 mm to about 20 mm. When wood biomass is utilized, the wood particles can be provided as a product known as "pin chips", in which elongate wood particles constitute the particulate, and the average, maximum lengths of the wood particles can provide the average, maximum dimensions disclosed above, or even greater dimensions. In some embodiments, large wood pin chip feedstock will be used, for example having average maximum lengths in the range of about 2 to 4 cm and potentially also an average width of about 0.2 to 1 cm. Such pin chip wood products, and other particulate wood products, can be free from bark, or can contain bark.

Besides mechanical processing as described above, the lignocellulosic feedstock may also be subjected to other processes to physically disrupt its native structure. Illustratively, the biomass can be steam exploded prior to use in the chemical or biological processes described herein.

The lignocellulosic biomaterial feedstock will usually contain some level of moisture prior to its combination with aqueous or other mediums as described herein. Moisture contents in the range of about 20% to about 70% by weight will be typical, depending upon the type of biomass, source, prior processing, and other factors. For wood biomass, the initial moisture content will typically be in the range of about 40% to 50% by weight.

It has been discovered that substantial hydrolytic liquefaction of particulate lignocellulosic biomass to provide flowable and pumpable digest slurries, even in highly aqueous mediums, can be cost effectively achieved. The liquefaction thus eases flow transport of the biomass and also reduces downstream material volume. In preferred liquefaction processes the processing medium is an aqueous medium containing one or more dicarboxylic acids, which mimics the action of an enzyme in the hydrolysis of components of the biomass. Thus, the use of enzymes, which can be expensive, in providing biomass liquefaction to an extent necessary for pump or flow operations, can be avoided or significantly reduced. A variety of dicarboxylic acids may be used alone or in combination in the liquefaction of the lignocellulosic biomass. Maleic acid (e.g. provided to the medium as maleic acid or maleic anhydride) and/or succinic acid (e.g. provided to the medium as succinic acid or succinic anhydride) and/or oxalic acid may be used in certain embodiments of the invention. Maleic acid is preferred from work to date.

To achieve liquefaction of at least a portion of the biomass, a mixture of the biomass with a liquid pretreatment medium containing the dicarboxylic acid(s) can be prepared. The liquid pretreatment medium is desirably aqueous, preferably at least about 60% by weight aqueous, more preferably at least about 80% by weight aqueous, and most preferably about 90% to about 99.9% by weight, or more, aqueous. The use of highly aqueous mediums avoids or minimizes the need to use other solvent materials, such as organic solvents, for the liquefaction. Such organic solvents would typically add significantly more material cost than water. In particularly beneficial embodiments, the pretreatment medium will be constituted 97% to 100% by weight of water and dicarboxylic acid(s).

In one mode of preparing a pretreatment medium, a dicarboxylic acid, or its corresponding acid anhydride, can be added to water to form an aqueous liquid dicarboxylic acid medium. The resulting aqueous solution of the dicarboxylic acid can then be combined with the biomass to form the mixture. In other modes, the biomass can be combined with added water, followed by addition of the dicarboxylic acid(s) or their corresponding anhydrides. These and other methods of preparing the initial biomass/medium mixture are contemplated as within the invention.

When a dicarboxylic acid is used, it is desirably present at a relatively low concentration in the overall mixture, for example in the range of about 0.1 to about 5% by weight relative to the weight of biomass solids dry matter, with this value more typically being in the range of about 0.1% to 2% by weight, and preferably in the range of about 0.1 to about 1% by weight. In certain particularly preferred processes, a dicarboxylic acid is present in the overall mixture at a concentration of about 0.2% to about 0.5% by weight relative to the biomass solids dry matter. Because it has been discovered that the aqueous dicarboxylic acid(s) can, through its/their hydrolytic action, substantially liquefy the biomass, the use of any other organic or inorganic reagents in the treatment solution can be avoided altogether or at least minimized. In certain embodiments, on a molar basis, the dicarboxylic acid(s) is the predominant (over 50%) protic organic substance in the solution of the starting biomass mixture, or constitutes at least 80% or at least 90% of the total protic organic substance(s) in the solution of the starting biomass mixture. The dicarboxylic acid(s) can be essentially the only protic organic substance(s) in or added to the starting biomass mixture, or essentially the only protic substance of any kind in or added to the starting biomass mixture (other than water, when an aqueous solution is used); it will be understood in these embodiments that trace amounts of organic or other protic substances may nonetheless be present as impurities (e.g. less than about 0.3% by weight). The use of the dicarboxylic acid(s) as the substantial or only hydrolytic reagent can avoid the use of other chemical reagents which add to material costs and potentially serve as or lead to the formation of inhibitors of later processing steps such as enzymatic hydrolysis and/or fermentation. It is contemplated that in certain embodiments, however, that ethanol may be included along with the dicarboxylic acid(s) in the starting biomass mixture, for example in certain processes at a level of about 0.5% to about 20% by weight relative to the weight of the dry biomass matter. When the dicarboxylic(s) acid digestion is a part of a process for producing ethanol such as described herein, a portion of the product ethanol can be diverted to the starting biomass mixture for these purposes. The presence of ethanol in such processes may for example be useful to result in a greater conversion of the biomass to dissolved substances and/or to better condition undissolved matter for subsequent treatment with a cellulase enzyme.

The dicarboxylic acid-containing liquid medium or other pretreatment medium can be combined with the biomass solids in any suitable ratio to facilitate achieving at least partial liquefaction of the solids. In some forms, the biomass and liquid medium will be combined in amounts to provide an overall liquids/solids mixture constituted at least about 3% by weight of the biomass solids on a dry weight basis, and typically in the range of about 3% to about 50% by weight. In certain preferred forms, the biomass solids will constitute at least about 10% by weight of the mixture on a dry weight basis, for example about 10% to about 40%, or at least about 15% by weight of the mixture on a dry weight basis, for example about 15% to about 35% or about 15% to about 25%.

When used, aqueous dicarboxylic acid(s) solutions to be combined with the biomass to form mixtures as described above can have any suitable concentration of the dicarboxylic acid(s). In certain processes, a starting aqueous dicarboxylic acid solution will include maleic acid and/or other dicarboxylic acid(s) at a total concentration in the range of about 10 mM to about 100 mM of the dicarboxylic acid(s).

The biomass can be incubated in contact with the dicarboxylic acid-containing liquid medium or other pretreatment medium at any temperature effective to provide at least partial liquefaction of the biomass. Elevated temperatures can be employed, for example a temperature greater than about 100° C., and typically in the range of about 100° C. to about 210° C. In certain processes, the biomass/liquid preparation will be subjected to heating within a temperature range of about 170° C. to about 210° C. In certain other processes, a relatively low temperature digestion will be conducted, with heating controlled within a temperature range of about 120° C. to about 155° C. Surprisingly, it has been found that in such low temperature digestions, even when using relatively long incubation times, such as greater than about 1 hour, e.g. 1 to 24 hours, the formation of sugar degradation products such as furfural and 5-hydroxymethylfurfural is very low, and the selectivity for xylose and glucose monomers is enhanced. The dicarboxylic acid(s) thus closely mimic the selective action of an enzyme which can be capitalized upon in low temperature processing, which is contrasted to the behavior of conventional inorganic acids such as sulfuric acid, which exhibit lower selectivity for the sugars under longer incubation periods at relatively low temperatures.

During the incubation, the biomass-containing mixture can be stirred or otherwise mixed to improve digestion of the biomass. However, it has been discovered that the dicarboxylic acid(s) can effectively liquefy the biomass even in the absence of mixing. Thus, in certain forms, incubations in the presence of the dicarboxylic acid(s) are performed partially or completely in the absence of mechanical mixing. This simplifies equipment needs for the operation, saves wear and tear, and avoids energy usage that would otherwise be needed to move the biomass, particularly in its initial unliquified state. Accordingly, in variants of the processes described herein, at least an initial unmixed dicarboxylic acid(s) incubation period is conducted to partially liquefy the biomass, for example a period of at least about 1 minute. Subsequent to the initial unmixed period, alternate forms can be completed with mixing, or without mixing, during the heated incubation period.

The incubation of the biomass in contact with the dicarboxylic acid-containing medium can be for any suitable period of time for at least partial liquefaction to form a digest slurry. In certain embodiments, the biomass/liquid mixture will be heated, e.g. within a temperature range disclosed above, for about 1 minute to about 60 minutes, more typically from about 3 minutes to about 30 minutes. Certain preferred embodiments will involve such heating of the biomass/liquid mixture for a period of about 3 minutes to about 15 minutes. As noted above, in other embodiments, longer incubation periods with the dicarboxylic acid(s), such as 1 to 24 hours, will be utilized under temperature conditions sufficiently low to achieve high selectivity for xylose formation, for example to provide (xylose+soluble xylose oligomer):furfural molar ratios in the digested medium above about 10, or above about 20. Such low temperature processes are conducted at a temperature in the range of about 120° C. to about 155° C. in certain embodiments.

Treatment of lignocellulosic biomass feedstock at appropriate concentrations, times and temperatures using dicarboxylic acid(s) may be used to achieve above about 70% hydrolysis of hemicellulose in the biomass to monomeric xylose, preferably above about 80%, and more preferably above about 90%. These treatments can also result in a total monomeric xylose content in the digest composition of at least about 10 g/L, more preferably at least about 15 g/L, and typically in the range of about 15 g/L to about 30 g/L. In some forms of practice, a liquefied fraction of biomass from a dicarboxylic acid(s) digestion, for example containing solubilized components as described herein, can be contacted with additional starting lignocellulosic biomass alone or with additional fresh dicarboxylic acid(s) solution to result in the hydrolysis of hemicellulose in the additional starting biomass and potentially a resultant liquefied fraction having an increased xylose monomer content as compared to the liquefied fraction from the initial digestion. The xylose in the digested medium, and potentially also smaller amounts of glucose therein, can then be fermented to ethanol as described herein. Such digestion processes can be conducted in batch or continuous modes, for example in some embodiments using countercurrent processing techniques for contact of new amounts of the biomass with the previously liquefied fraction alone or combined with fresh maleic acid solution, and/or wash solution if needed or desired. The unliquefied large particulate matter resultant of such processes, substantially depleted of hemicellulose but enriched in cellulose, can constitute a significant weight fraction of the digest slurry. For example, the undissolved solid particulates of the digest slurry composition can be comprised at least 10% by weight, on a dry weight basis, of particles having a maximum dimension greater than about 1 cm; typically, this number can be in the range of about 10% to about 30%. The undissolved large particulate in the digest slurry can be processed with cellulase enzymes to form sugars for fermentation to ethanol as described herein, or can be separated, dried and put to other use, such as for its fuel value by burning the material to generate heat that is at least in part fed to the dicarboxylic acid(s) digestion process. In the latter case an ethanol biofuel operation based completely or primarily on xylose fermentation can be provided.

At the completion of the liquefaction treatment with the dicarboxylic acid(s), the resulting composition will typically be characterized as a mixed, acidic liquid/solid composition having significantly more flowable liquid material than the initial mixture, with the flowable liquid material including the dicarboxylic acid(s), dissolved xylose and glucose monomers derived from digestion of the biomass, and suspended finely divided biomass particles that flow freely with the liquid material. The flowable liquid material can also include minor amounts of furfural from the degradation of xylose and 5-hydroxymethylfurfural (HMF) from the degradation of glucose, and/or phenolic compounds liberated or formed from the biomass. The dicarboxylic acid(s) liquefaction will desirably be controlled to keep the formed furfural to less than about 8 g/L, more preferably less than about 5 g/L, and/or the formed HMF to less than about 5 g/L, more preferably less than about 2 g/L. As discussed above, the overall treated composition will typically also include some larger, partially-digested particles of the biomass which are enriched in lignin and glucan and which do not suspend and flow freely with the liquid portion of the composition, such that they can readily be separated even without filtration, by pouring or otherwise draining off the liquid portion of the treated overall composition, e.g. by centrifugation, to leave behind the larger particle material.

The dicarboxylic acid(s) digest process can be conducted to cause a substantial increase in the bulk density of the biomass solids dry matter. For example, the digestion can be conducted to as to increase the bulk density of the biomass dry matter by at least about 15%, more preferably at least about 30%. As will be understood, these increases in solids bulk density also provide a reduction in the volume of the wet mixture during the processing. In addition or alternatively, a substantial percentage of the original biomass dry matter can be converted to solubilized components during the dicarboxylic acid(s) digestion. For instance, in certain embodiments at least about 10% of the original biomass dry matter is converted to solubilized solids by the dicarboxylic acid(s) digestion, more preferably at least about 30%, and typically in the range of 20% to about 45%. Correspondingly, the digest slurry compositions resultant of such processes can in some aspects have an undissolved solids content (including both large particles and finely divided solids) of at least about 55% by weight, on a dry weight basis, and in certain embodiments about 55% to about 90%.

After the heated dicarboxylic acid(s) digestion for liquefaction, the resulting digest slurry can be processed as further described herein and/or as described in U.S. Patent Application Ser. No. 61/369,474, entitled "Biomass Liquefaction Processes, and Uses of Same," filed on Jul. 30, 2010, and PCT International Application No. PCT/2011/045973, filed on Jul. 29, 2011, and hereby incorporated herein by reference, which describes downstream enzymatic hydrolysis and fermentation processes that can be used in conjunction with the liquefaction and heat recovery processes described herein.

In one mode of use, at least a portion of the digest slurry formed by the pretreatment liquefaction process, including partially-digested lignocellulosic biomass particles and some of the flowable liquid material, and potentially the entirety of the digest slurry, is subjected to enzymatic hydrolysis to further liquefy the composition. Where the digest slurry formed is acidic, and an enzyme is used that is inactive or insufficiently active at the acidic pH of the slurry, the pH of the slurry can be increased (i.e. the composition can be neutralized) to a level suitable for the enzyme, for instance a pH in the range of about 4 to 7 at which the enzyme is active. Any suitable basic substance can be used for such neutralization, such as an alkali or alkaline earth metal hydroxide such as sodium hydroxide and/or calcium hydroxide, and/or ammonium hydroxide. Such a neutralized composition will typically thereby contain, in solution, cations and anions of a corresponding salt(s) of the dicarboxylic or other acid used for the hydrolytic liquefaction of the original biomass feedstock. Surprisingly, it has been discovered that the enzymatic hydrolysis process can be conducted to good effect on the digest slurry without prior removal of potentially inhibitory components such as furfural, HMF, phenols and/or other compounds from the composition by washing or other means.

The enzymatic hydrolysis can be conducted with a cellulase enzyme. In this regard, a cellulase enzyme is an enzyme that catalyzes the hydrolysis of cellulose to products such as glucose, cellobiose, and/or other cellooligosaccharides. Cellulase enzymes may be provided as a multienzyme mixture comprising exo-cellobiohydrolases (CBH), endoglucanases (EG) and beta-glucosidases (betaG) that can be produced by a number of plants and microorganisms. The process of the present invention can be carried out with any type of cellulase enzymes, regardless of their source; however, microbial cellulases provide preferred embodiments. Cellulase enzymes can, for example, be obtained from fungi of the genera *Aspergillus, Humicola*, and *Trichoderma*, and from the bacteria of the genera *Bacillus* and *Thermobifida*.

The initial liquefaction pretreatment of the biomass has been found to condition the remaining, partially-digested particulate material in a fashion that renders it more susceptible to the action of cellulase enzymes which digest cellulose present to form glucose and soluble gluco-oligomers. While any suitable enzyme loading can be used to further treat the biomass composition or its undigested components, for example a loading in the range of up to about 20 FPU (Filter Paper Units)) (Adney, W. and Baker, J. "Measurement of Cellulase Activities," Laboratory Analytical Procedure (LAP) 006, National Renewable Energy Laboratory, 1996) of enzyme per gram of glucan in the original biomass feedstock (prior to the liquefaction pretreatment), it has been discovered that low enzyme levels can be effectively used and thus cellulase enzyme loadings less than about 3 FPU per gram of original glucan are desirably used, preferably less than 2 FPU per gram of original glucan, and in certain embodiments about 1.5 FPU or less per gram of original glucan, wherein in each of these cases a minimum of about 0.1 FPU per gram of original glucan can optionally be employed. In certain preferred embodiments, a low cellulase enzyme loading in the range of about 0.5 FPU to about 1.5 FPU per gram of original glucan is used. These low loadings provide significant material cost savings due to the expense of the relevant enzymes. In terms of milligrams of cellulase enzyme per gram dry matter of original biomass, the cellulase enzyme can be used again at any suitable level, for example at a loading in the range of up to about 10 mg of enzyme per gram of original biomass feedstock. Again, however, low enzyme levels can be effectively used and thus such cellulase enzyme loadings less than about 3 mg of enzyme per gram of original biomass are desirably used, preferably less than 2 mg enzyme per gram of original biomass, and more preferably less than about 1.5 mg enzyme per gram of original biomass, wherein in each of these cases a minimum of about 0.1 mg enzyme per gram of original biomass can optionally be employed. In certain preferred embodiments a low cellulase enzyme loading in the range of about 0.3 mg to about 1 mg enzyme per gram of original biomass dry matter is used.

The enzyme hydrolysis process can be conducted for a suitable duration to achieve significant conversion of cellulose from the biomass to monomeric glucose. Durations may for example be from about 1 hour up to about 72 hours, more typically in the range of about 6 hours to about 36 hours, and in some embodiments about 10 to 30 hours. Such processes can be conducted in any suitable vessel, including for example stirred tank fermentation vessels. Such processes can be conducted so as to achieve conversion of at least about 15% by weight of the original cellulose to monomeric glucose, an in more beneficial processes at least about 50% by weight, for instance in the range of about 50% to about 100% by weight.

Hydrolytic treatment of lignocellulosic biomass sequentially with an acid, preferably a dicarboxylic acid(s), and an enzyme(s) as described herein can not only provide an effective conversion of the biomass to monomeric sugars including glucose and/or xylose, but can also yield a liquefied, flowable biomass preparation with beneficial rheological properties for subsequent processing operations. In this regard, it is known that concentrated biomass slurries encountered in prior art processing have been highly viscous, strongly shear-thinning materials, exhibiting high levels of concentration-dependent yield stress (the stress at which a material begins to deform plastically). This imposes power requirements upon pumps, mixers and other processing equipment typically used in biomass conversion, since these devices must have sufficient power to overcome the yield stress of the material to cause its movement. Preferred initial digest slurries prepared non-enzymatically as described herein, typically by acid-catalyzed liquefaction, will exhibit yield stresses lower than their corresponding starting biomass solids-liquid mixture, more preferably less than about 15000 Pascals, and in the range of about 10000 Pascals to 15000 Pascals in some embodiments. In further embodiments, preferred biomass slurry compositions treated sequentially with non-enzymatic and then enzymatic hydrolysis as described herein will exhibit yield stresses of less than about 3000 Pascals, more preferably less than about 1000 Pascals. In the applicants' work, such yield stresses have been determined by extrapolating shear rate versus shear stress using the Bingham model: $\tau=\eta_p\gamma+\tau_y$; where $\tau$=shear stress (Pa); $\gamma$=shear rate (1/s); $\tau_y$=Bingham yield stress (Pa); and $\eta_p$=plastic viscosity (Pa·s). Additional details are found in Example 6 below, and can also be found in Howard A. Barnes, *The yield stress-a review-everything flows?*, J. Non-Newtonian Fluid Mech. Vol. 81, 133-178 (1999).

The treated biomass preparation resultant of the initial dicarboxylic acid treatment or resultant of such treatment in combination with an enzymatic hydrolysis can be processed by fermentation or otherwise to yield useful products, including biofuel products. In preferred forms, monomeric sugar(s) at either of these treatment stages can be charged directly or indirectly to a fermentation process for conversion to organic substances, especially ethanol.

In certain embodiments, the biomass feedstock is fed through both the pretreatment liquefaction/heat recovery and subsequent enzymatic hydrolysis without any fractionation, and thereafter the flowable, liquefied material is separated from the remaining partially-digested biomass solids, for example by centrifugation. The liquefied material, which in some embodiments comprises at least about 3% by weight monomeric pentose sugars (e.g. xylose) and typically about 3% to about 6%, is then charged to a fermentation unit for conversion of the xylose and/or other pentose sugars, and potentially also glucose (usually at a lower concentration, e.g. less than about 2% by weight), to ethanol. The fermentation of the sugar(s) to produce ethanol can be conducted with any of a wide variety of fermentive microorganisms such as yeast or bacteria, including genetically modified versions thereof, and using known techniques. The ethanol can then be purified from the fermented medium, for example by distillation. The solids material recovered from the separation can be subjected to further hydrolytic treatment by acid(s) or enzymes to reduce biomass components to provide additional amounts of monomeric sugars such as xylose and/or glucose can be fermented to provide ethanol which can be recovered for example by distillation, all as described above. In a preferred embodiment, the recovered solids are first subjected to acid-catalyzed liquefaction, preferably with a dicarboxylic acid(s), for example under conditions and with heat recovery and recycle to newly charged biomass as described hereinabove, and a clear liquid fraction (essentially free of suspended solids) containing sugars, typically predominant in xylose but also potentially containing other pentoses and glucose, can be separated from the remaining solids and fermented to ethanol. Such fermentations can be conducted as described above. The remaining solids from the second dicarboxylic acid(s) treatment can then be neutralized as appropriate and hydrolyzed with an enzyme to yield glucose, which can be fermented to ethanol. This enzyme hydrolysis can be conducted under conditions as described hereinabove, but in preferred embodiments is conducted using consolidated bioprocessing in which enzyme hydrolysis and fermentation are conducted simultaneously. Such consolidated bioprocessing achieves simultaneous saccharification and fermentation (referred to as "SSF") of the biomass material using yeast or another microorganism(s) that expresses a cellulolytic enzyme(s) as well as converts the glucose (and potentially also xylose) to ethanol, or a yeast or other microorganism(s) that is thermotolerant and can effectively ferment the sugar(s) in the presence of added cellulase enzyme(s).

In this regard, suitable microorganisms for such SSF processing or conventional fermentation processing include for example genetically-modified or non-genetically-modified yeast, including for example *Saccharomyces cerevisiae*. Other yeasts for fermentation may include pentose fermenting yeast, cellulose fermenting yeast, cellulobiohydrase- and/or endoglucanase expressing yeast, *Clostridium thermocellum* or *Thermoanaerobacterium saccharolyticum*, either of which has been genetically modified to ferment glucose, xylose, and/or cellulose to ethanol, thermotolerant strains of yeast such as *Saccharomyces cerevisiae* SERI strain ($D_5A$), *Saccharomyces uvarum*, *Candida* genera *acidothermophilium*, *brassicae*, and *lusitaniae*, *Brettanomyces clausenii* (Y-1414), *Kluyveromyces marianus*, and others. At the conclusion of the consolidated bioprocessing, the fermented medium can be charged to a separator such as a stripper unit to separate the solids (rich in lignin) from a liquid medium containing the ethanol, and the liquid medium can be processed to purify the ethanol such as by distillation.

In additional embodiments, a biomass digest composition resultant of the acid(s)-catalyzed liquefaction with heat recovery and subsequent enzymatic hydrolysis can be fermented as a whole in a single fermentation, desirably utilizing a microorganism such as a yeast that can convert both xylose and glucose to ethanol, or a combination of microorganisms to accomplish this goal. Such a fermentation may also be an SSF process as described above, achieving hydrolysis of glucan to glucose simultaneously with fermentation of the glucose (and potentially also xylose) to ethanol. Still other modes of use of the dicarboxylic acid(s) digest composition or the follow-on enzymatic digest composition to produce ethanol or other useful organic products will be apparent to those of ordinary skill in the art from the descriptions herein.

In still further aspects, when a dicarboxylic acid(s) such as maleic acid is used, at least a portion of the dicarboxylic acid(s) used in treating the biomass can be recovered and recycled to treat additional amounts of biomass, for example as described in U.S. Patent Application Ser. No. 61/251,034 filed Oct. 13, 2009 entitled "PROCESS FOR PREPARING ENRICHED GLUCAN BIOMASS MATERIALS," and which is hereby incorporated herein by reference in its entirety. Thus, in ethanol production processes described herein, after ethanol has been recovered from the neutralized fermentation material by, for example distillation, the material remaining is rich in the dicarboxylic acid. The dicarboxylic acid can then be recovered from this material, for example, by distillation. Once the recovery step is complete, the dicarboxylic acid can be recycled to the front of the process to treat additional amounts of lignocellulosic biomass. If desired, the distillation can be carried out under a vacuum in order to minimize formation of salts in the bottoms from the distillation column and also preserve the activity of the dicarboxylic acid. For example, maleic acid has a high boiling point and is stable up for periods of 10 to 60 min at 220° C., and stable for 24 hours or more at temperatures below 130° C. when dissolved in water. This dicarboxylic acid may be recovered and concentrated in the bottoms stream of the fermentation distillation column itself. Further evaporation would then give a concentrated maleic acid stream which would then be recycled to the front end of the process for further treatment of additional lignocellulosic biomass.

For the purpose of promoting a further understanding of certain inventive embodiments, as well as their features and advantages, the following specific Examples are provided. It will be understood that these Examples are illustrative, and not limiting, of the invention.

Example 1

Liquefaction of Mixed Hardwood Under Varied Conditions

This example demonstrates substantial liquefaction of mixed hardwood pin chips under various temperature and time conditions, corresponding to varied Severity Factors, using an aqueous solution of maleic acid at a maleic acid concentration of 1% wt/wt relative to the hardwood pin chips (dry weight basis). As used in the Figures and elsewhere herein in reference to a biomass treatment, "Severity Factor"=$\log(R_o)=\log \{t \cdot \exp[(T-100)/14.75]\}$, where t is residence time in minutes, exp is exponent, and T is the target reaction temperature in ° C. Samples (50-100 g each) of the mixed hardwood pin chips (average particle length about 0.5-1.0 inch) were soaked in the maleic acid solution overnight at solids loadings of 15% (see digital image of a thus-prepared sample in FIG. 3). The next day, in a sealed reaction vessel, the slurry was preheated to 140° C. for 10 minutes (essentially no reaction occurring) and then moved to a sandbath heated to the target temperature (190, 195, 200, 205, or 210° C.). The samples were then given a heat-up time of 5 minutes and then kept in the sandbath for an additional period of 5, 10, 15, 20 or 30 minutes. The runs are summarized in Table 1 below.

TABLE 1

| Temperature (Celcius) | Reaction Time (min) | Heat up time (min) | Total time (min) | Maleic acid conc (%) wt/wt dry biomass | % Solids Loading |
|---|---|---|---|---|---|
| 190 | 10 | 5 | 15 | 1 | 15% |
| 200 | 5 | 5 | 10 | 1 | 15% |
| 200 | 10 | 5 | 15 | 1 | 15% |
| 205 | 5 | 5 | 10 | 1 | 15% |
| 210 | 5 | 5 | 10 | 1 | 15% |
| 195 | 20 | 5 | 25 | 1 | 15% |
| 200 | 15 | 5 | 20 | 1 | 15% |
| 205 | 10 | 5 | 15 | 1 | 15% |
| 210 | 10 | 5 | 15 | 1 | 15% |
| 200 | 20 | 5 | 25 | 1 | 15% |
| 210 | 30 | 5 | 35 | 1 | 15% |

Figure 3:
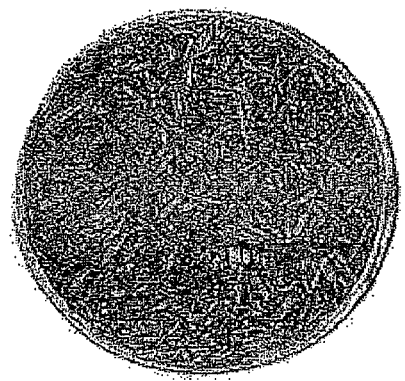
FIG. 3 is a digital image showing an initial, unheated mixture of aqueous maleic acid and particulate wood biomass at 15% solids loading (dry weight).
Figure 4:
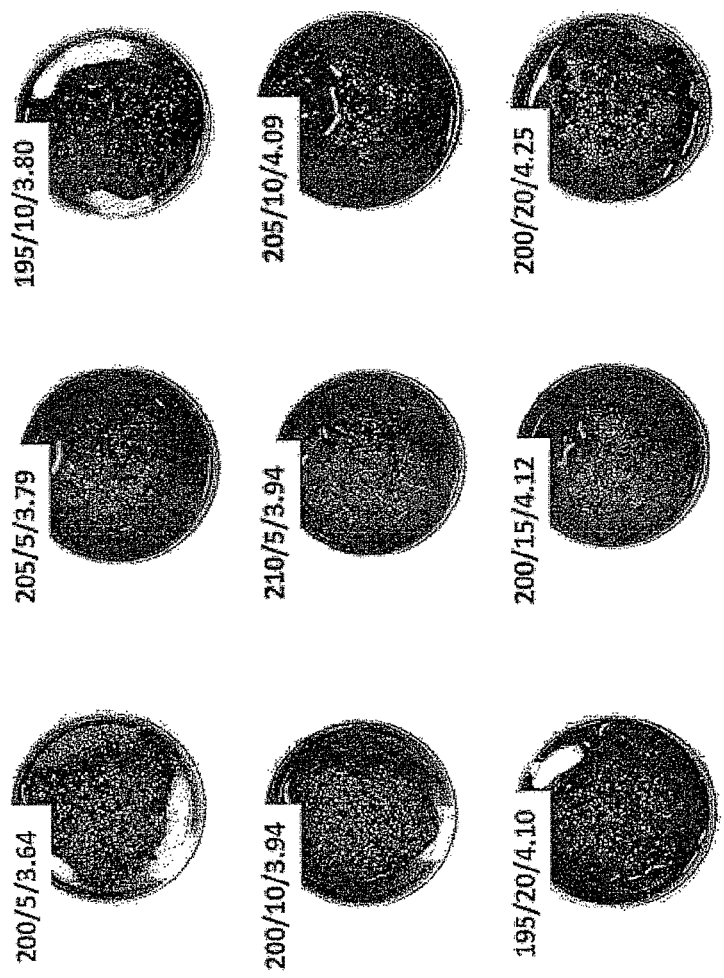
FIG. 4 is a digital image showing biomass digest slurries prepared by heating mixtures as in FIG. 3 at varying time and temperature conditions for liquefaction, as described in Example 1.
Figure 5:
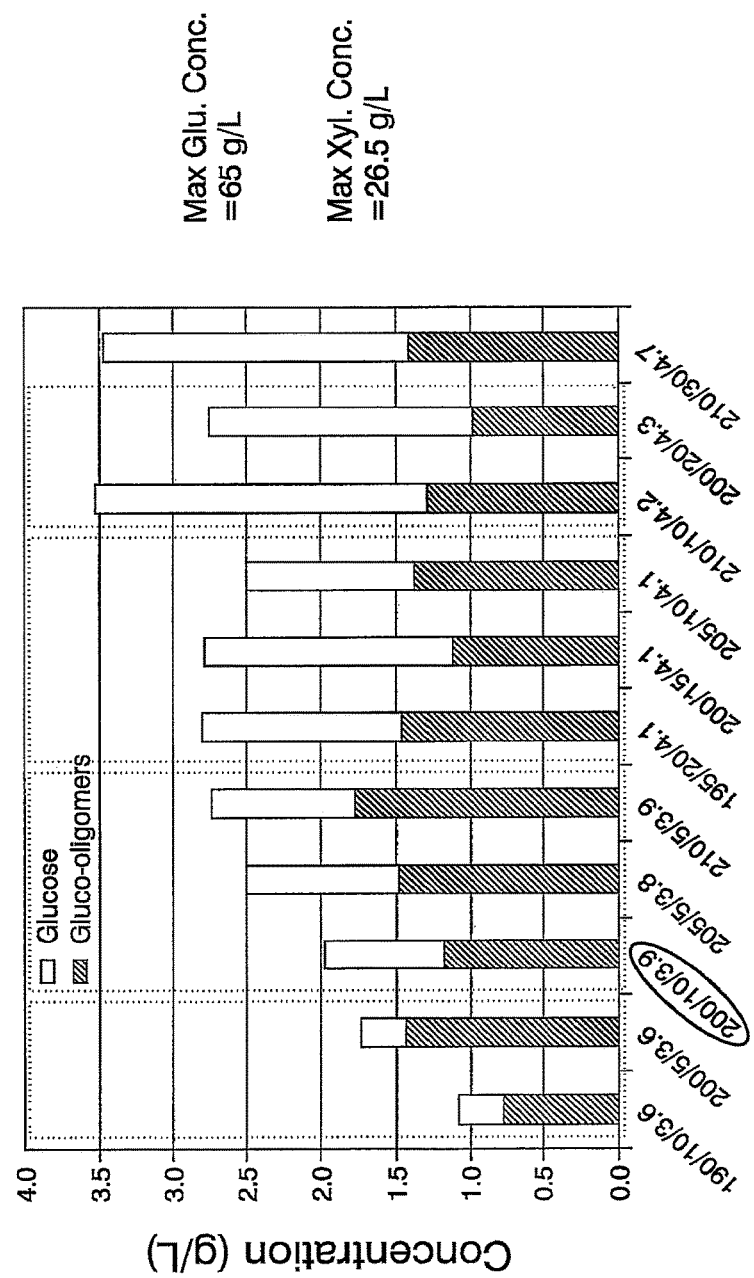
FIG. 5 provides a graph of glucose and gluco-oligomer concentration in digest slurries depicted in FIG. 4 and prepared as in Example 1.
Figure 6:
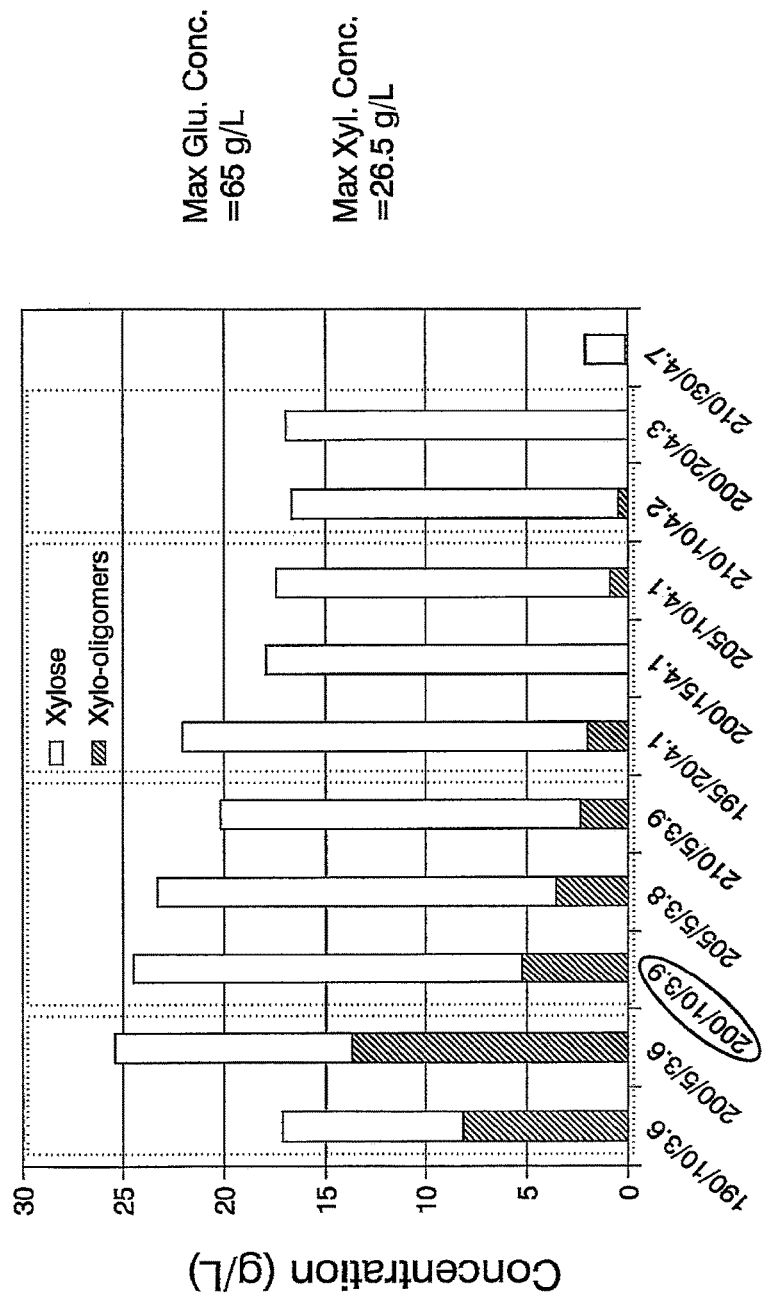
FIG. 6 provides a graph of xylose and xylo-oligomer concentration in digest slurries depicted in FIG. 4 and prepared as in Example 1.
Figure 7:
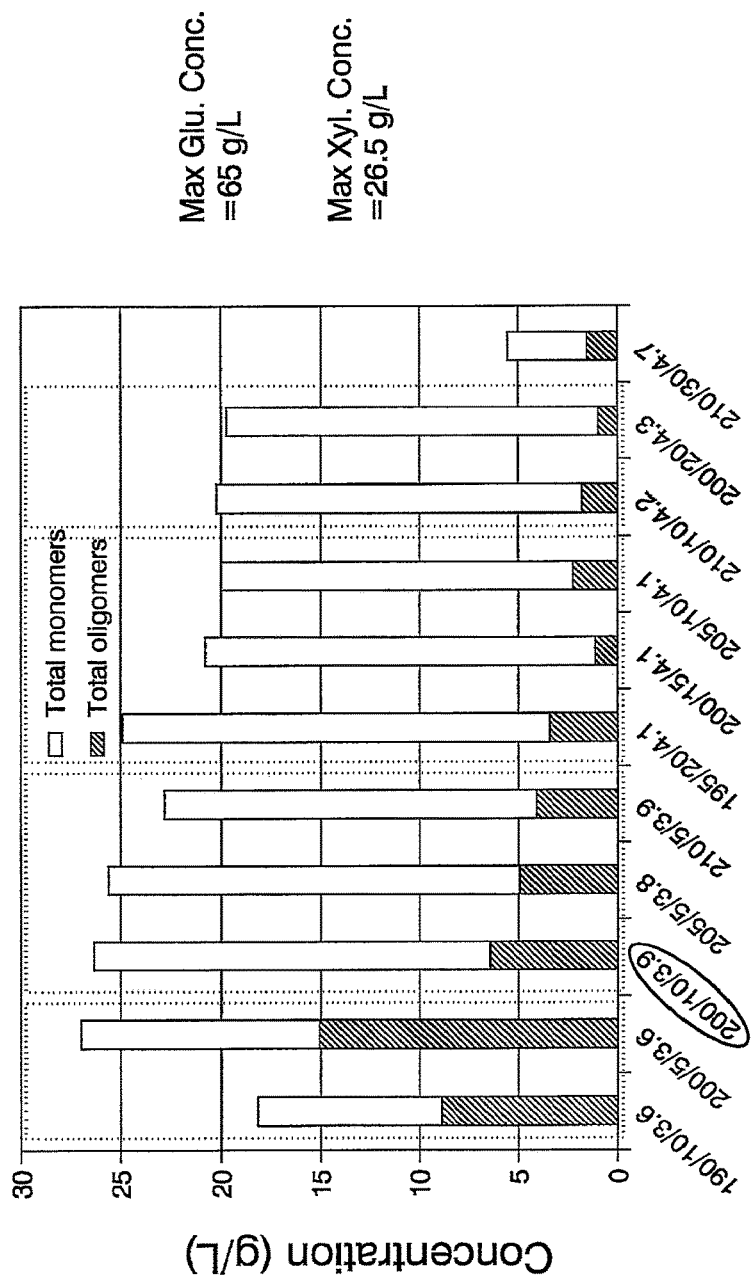
FIG. 7 provides a graph of total glucose and xylose monomer concentration in digest slurries depicted in FIG. 4 and prepared as in Example 1.

The treated samples were observed for signs of liquefaction and many photographed, and liquefied fractions of the samples were assayed for concentrations of sugar monomers (glucose and xylose) and soluble oligomers, and for 5-hydroxymethylfurfural (HMF) and furfural as degradation products of the sugars. FIG. 4 shows digital images of photographs taken of many of the samples, demonstrating significant liquefaction of the samples under the conditions tested as compared to the initial pretreatment medium/biomass mixture (FIG. 3). The digested slurries include substantial amounts of solids-rich liquid, typically brown or brown-black in color, and some relatively large undigested biomass particulates that readily separate from the liquid by simple pouring or other flow operations. The results of the compositional analyses are shown in FIGS. 5-7. FIGS. 5 and 6 show the concentrations of glucose and its oligomers and xylose and its oligomers, respectively, for the runs. As shown, the higher temperature runs gave generally higher conversion to glucose and xylose monomers, with the monomer levels decreasing in some of the highest temperature, longer runs, due to degradation of glucose to HMF and xylose to furfural. This degradation is also exhibited in FIG. 10 which charts correspondingly increased levels of furfural and HMF for the more severe runs. Total monomers and oligomers formed are shown in FIG. 7. From these and the other results it was demonstrated that highly advantageous liquefaction of the biomass occurred within the temperature/time conditions tested, particularly in those runs where the temperature was held at about 195-200° C. for periods of about 5-15 minutes. In corresponding runs conducted at an initial loading of 35% solids, the observed liquefaction was much lower, although reagent and/or physical processing parameters could be adjusted to improve results at these higher loadings.

Example 2

Enzyme Hydrolysis of Mimetic-Digested Biomass

Figure 8:
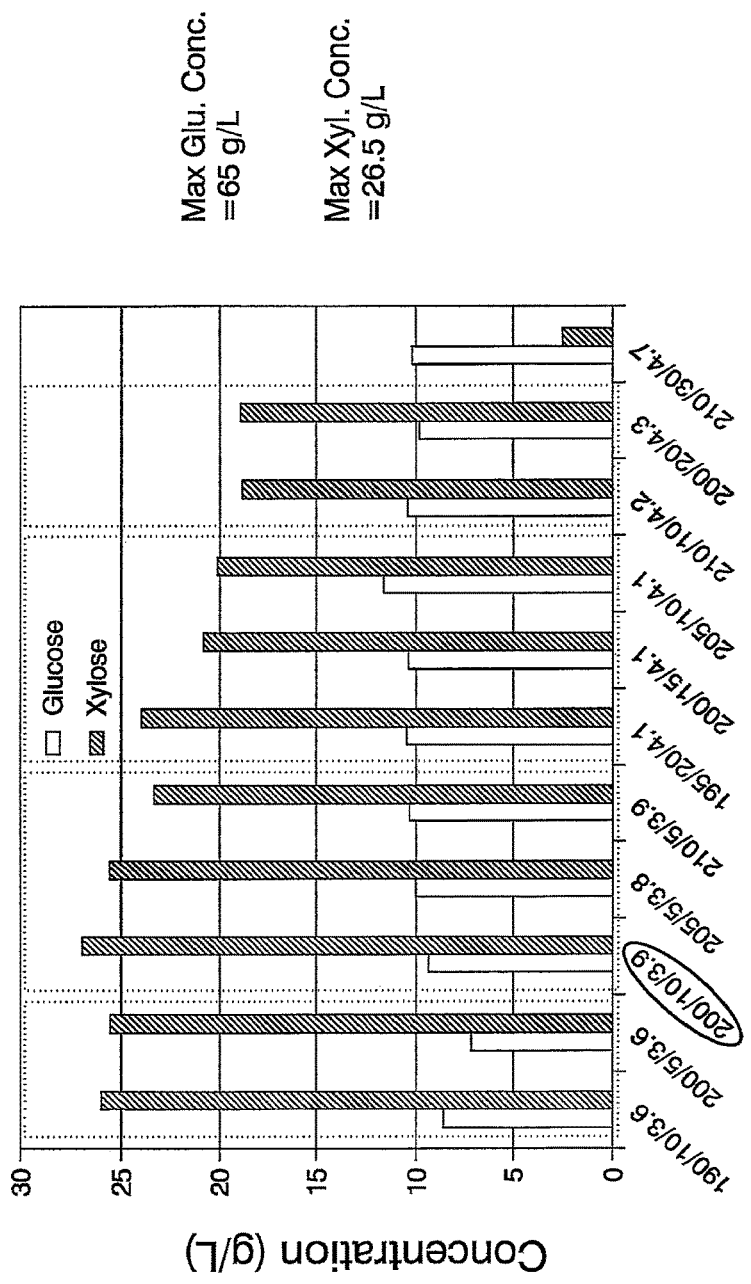
FIG. 8 provides a graph of glucose and xylose concentrations from a dual-step digestion including treatment of 15% dry solids of mixed hardwood with 1% maleic acid under varied temperature/time conditions followed by neutralization and a 24-hour cellulase digestion with 1 mg protein per gram of total dry solids biomass charged to the process, as described further in Example 2.
Figure 9:
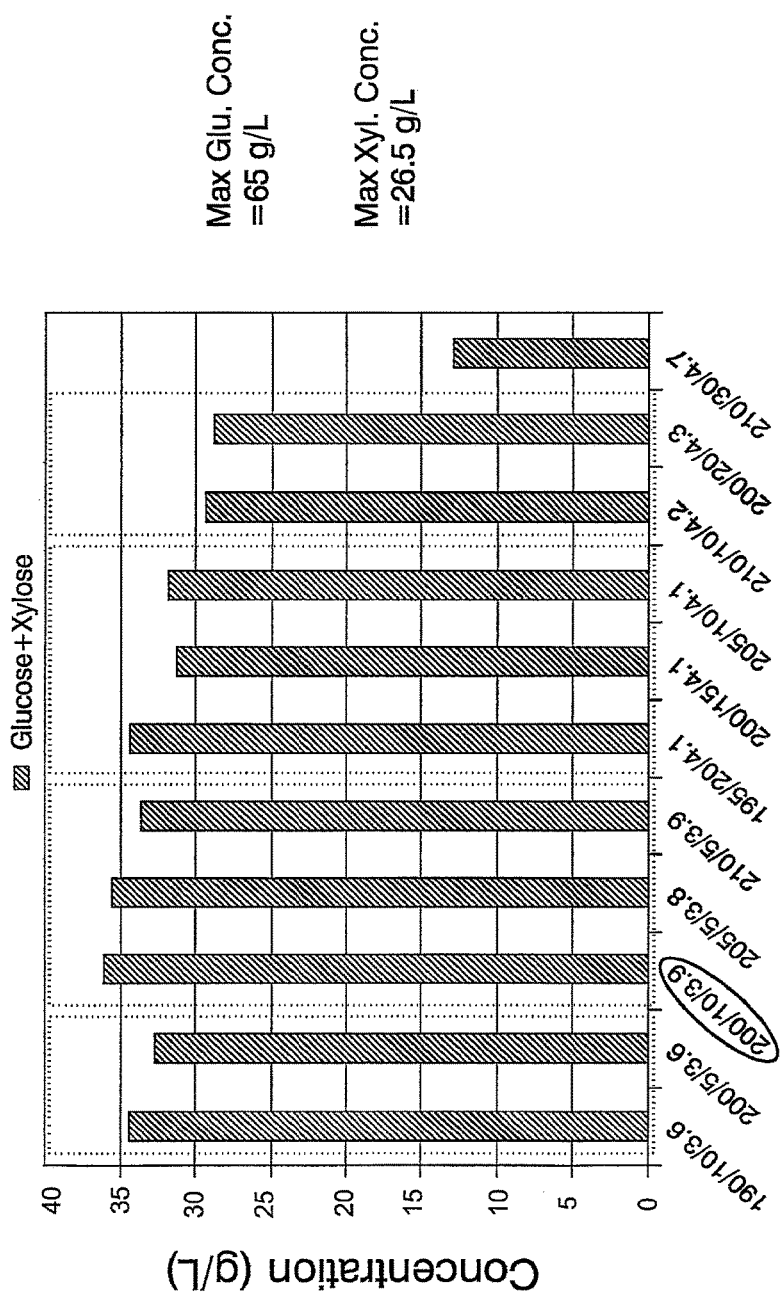
FIG. 9 provides a graph of total monomeric glucose and xylose concentration from the dual-step digestions plotted in FIG. 8 and described in Example 2.
Figure 10:
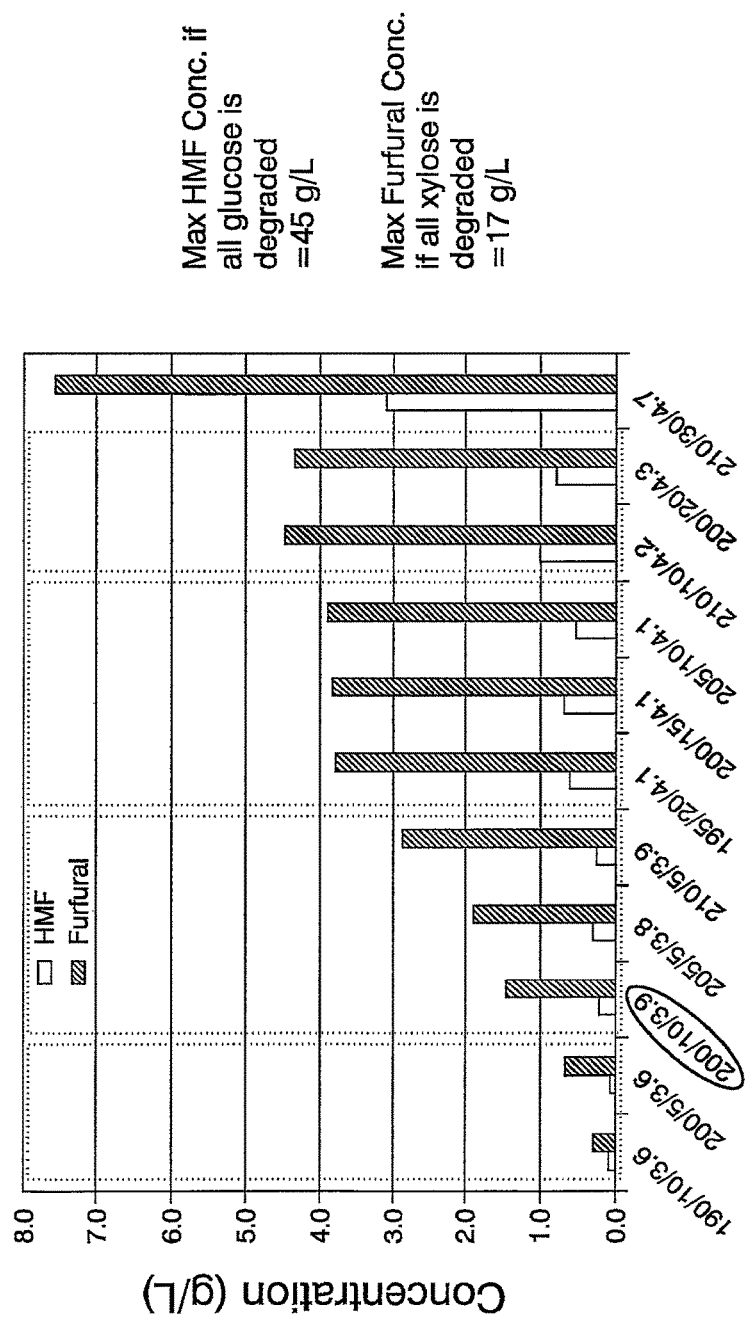
FIG. 10 provides a graph of 5-hydroxymethyl-furfural (HMF) and furfural concentrations for the dual-step digestions plotted in FIG. 8 and described in Example 2.

This example demonstrates a dual-step digestion including treatment of 15% dry solids of mixed hardwood with 1% maleic acid under varied temperature/time conditions as in Example 1 followed by neutralization and a 24-hour cellulase digestion with 1 mg protein per gram of total dry solids biomass charged to the process. The resulting digests as a whole were neutralized with ammonium hydroxide and charged respectively to a 250 mL Nalgene plastic bottle with cellulase enzyme (Spezyme CP (Genencor, A Danisco Division); Novozyme 188 (Novozyme); Multifect Pectinase (Genencor, A Danisco Division)) at 1 mg enzyme per gram of total starting biomass solids (dry weight). Enzyme hydrolysis was conducted for 24 hours at 50° C., pH 4.8, with stirring at 200 rpm, with samples taken at various intervals to measure glucose, xylose, furfural and HMF concentrations. The results are shown in FIGS. 8, 9 and 10. As shown in FIG. 8, the yields of glucose monomer (primarily from enzymatic hydrolysis of glucan) and xylose monomer (primarily from pretreatment) after the 24 hour incubation period were significant in all cases, with lower glucose concentrations occurring under the conditions of least severity (e.g. 190° C./10 minutes and 200° C./5 minutes) and significant levels of sugar degradation occurring at the most severe (210° C./30 minutes) conditions. Relatedly, as shown in FIG. 9, the total monomeric sugar formation was lowest in the least severe runs, and in the most severe runs sugar degradation impacted remaining yields of glucose and xylose. FIG. 10 shows that the corresponding formation of furfural and HMF from sugar degradation increased with increasing severity of conditions over the values tested.

Example 3

Enzyme Hydrolysis of Mimetic-Digested Biomass

Figure 11:
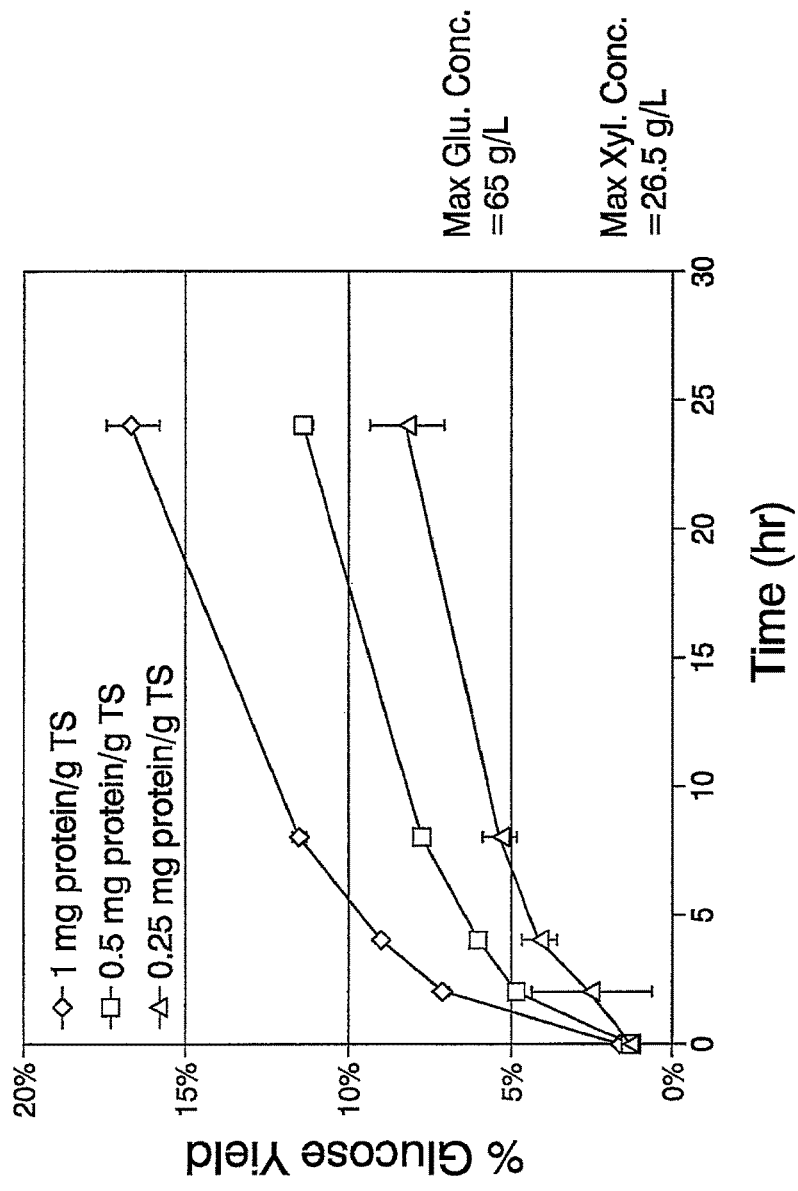
FIG. 11 provides a graph of monomeric glucose yields from dual-step digestions including treatment of 15% dry solids of mixed hardwood with 1% maleic acid under varied temperature/time conditions followed by neutralization and 24-hour cellulase digestions with 1, 0.5 and 0.25 mg protein per gram of total dry solids of biomass charged to the process, as described further in Example 3.
Figure 12:
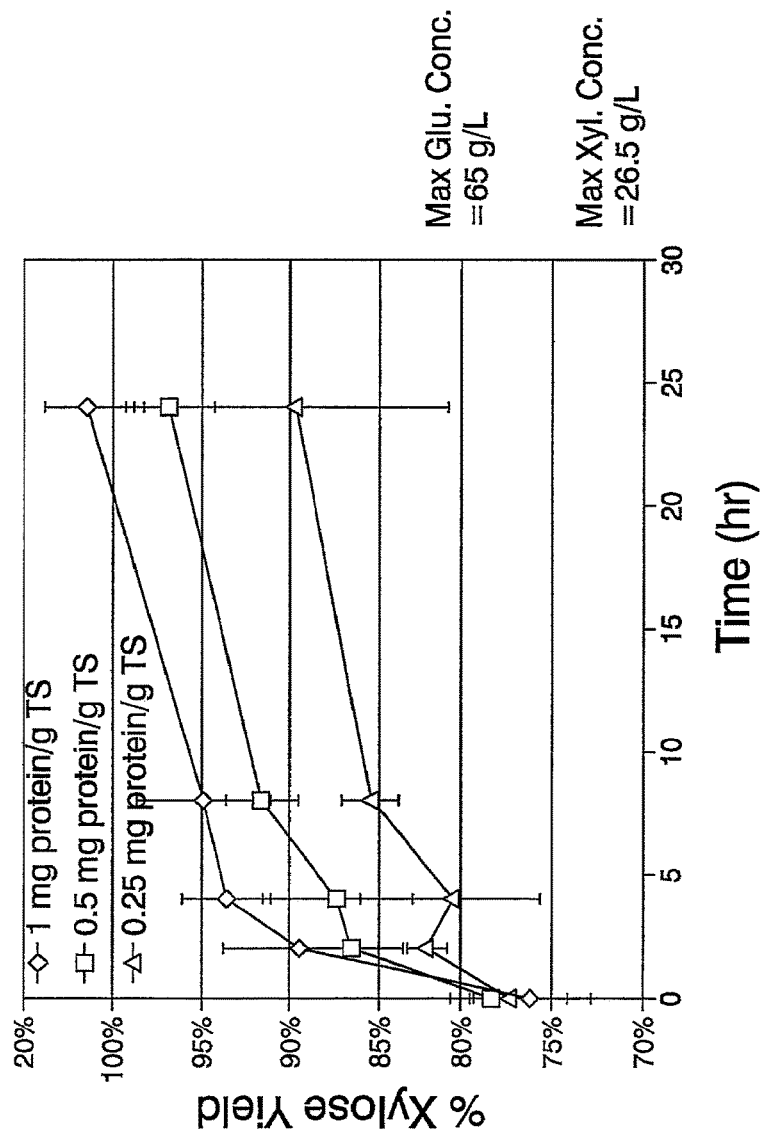
FIG. 12 provides a graph of monomeric xylose yields from the dual-step digestions plotted in FIG. 11 and described in Example 3.

This example demonstrates the enzymatic hydrolysis, at varied doses, of an overall biomass digest composition prior treated with a dicarboxylic acid (maleic acid). Mixed hardwood pin chip samples were digested as in Example 1 using the 5-minute heat-up, 10-minute treatment at 200° C. (1% Maleic Acid). The resulting digests as a whole exhibited enhanced, flowable properties and yield stress values much lower than that which would be measured in starting biomass/liquid mixture (see Example 4 and particularly FIG. 14, yield stress values at "0" enzyme hydrolysis time: consistently in the range of 13000 to 14000 after the maleic acid digestion). The digested samples were neutralized with ammonium hydroxide and charged respectively to a 250 mL Nalgene plastic bottle reactor with varying doses of cellulase enzyme (Spezyme CP (Genencor, A Danisco Division); Novozyme 188 (Novozyme); Multifect Pectinase (Genencor, A Danisco Division); 0.25 mg, 0.5 mg, or 1 mg enzyme per gram of total biomass solids, corresponding to about 0.375 FPU, 0.75 FPU and 1.5 FPU per gram of glucan in the raw biomass starting material). Enzyme hydrolysis was conducted for 24 hours at 50° C., pH 4.8 citrate buffer, with stirring at 200 rpm, with samples taken at various intervals to measure glucose concentration. The results are shown in FIGS. 11 and 12. As shown in FIG. 11, the yield of glucose monomer (from enzymatic hydrolysis of glucan) after a 24 hour incubation period increased with increasing enzyme loading over the ranges tested, with all runs exceeding about 7% yield of glucose monomer after the 24 hour incubation, and total yields in excess of 10% being readily attainable during this period. Similarly, as shown in FIG. 12, the additional yield of monomeric xylose after the 24 hour incubation period increased with increasing enzyme loading, and in all runs exceeded 85% total yield after the combined mimetic and enzyme treatments, with total yields of about 90% to 100% being readily attainable after the 24 hour enzyme treatment. For purposes of these yield calculations, the total xylose and glucose available in the starting biomass feedstock was taken as 19 g xylose/100 g initial solids and 42 g glucose/100 g initial solids, respectively.

Example 4

Rheologic Properties of Liquefied Biomass

This example demonstrates that a digest composition of mixed hardwood resultant of sequential dicarboxylic acid (maleic acid) and enzyme hydrolysis exhibits advantageous rheologic properties for downstream unit operations. Samples of steam-exploded, mixed hardwood were subjected to sequential maleic acid and enzyme hydrolysis as described in Example 3, except using 20% by weight biomass solids instead of 15%, and using varied enzyme digestion periods of 2, 4, 8 and 24 hours. The entire resulting biomass digest composition was tested for rheologic properties with a Rheometer ARG2 (TA Instruments, Inc.) as follows.

For the viscosity measurement, a steady state flow step was selected from the instrument setting. Approximately 5-10 mL of the sample was placed between two parallel plates with 1000 micrometer gap between the plates. A 20 mm diameter plate was used as the uppler plate. All measurements were conducted at 25° C. Shear rate (1/s) was varied from 0.5 to 10. Yield stresses have been determined by extrapolating shear rate versus shear stress using the Bingham model (Barnes, J. Non-Newtonian Fluid Mech. Vol. 81, 133-178 (1999)): $\tau=\eta_p\gamma+\tau_y$; where $\tau$=shear stress (Pa); $\gamma$=shear rate (1/s); $\tau_y$=Bingham yield stress (Pa); and $\eta_p$=plastic viscosity (Pa·s).

Figure 13:
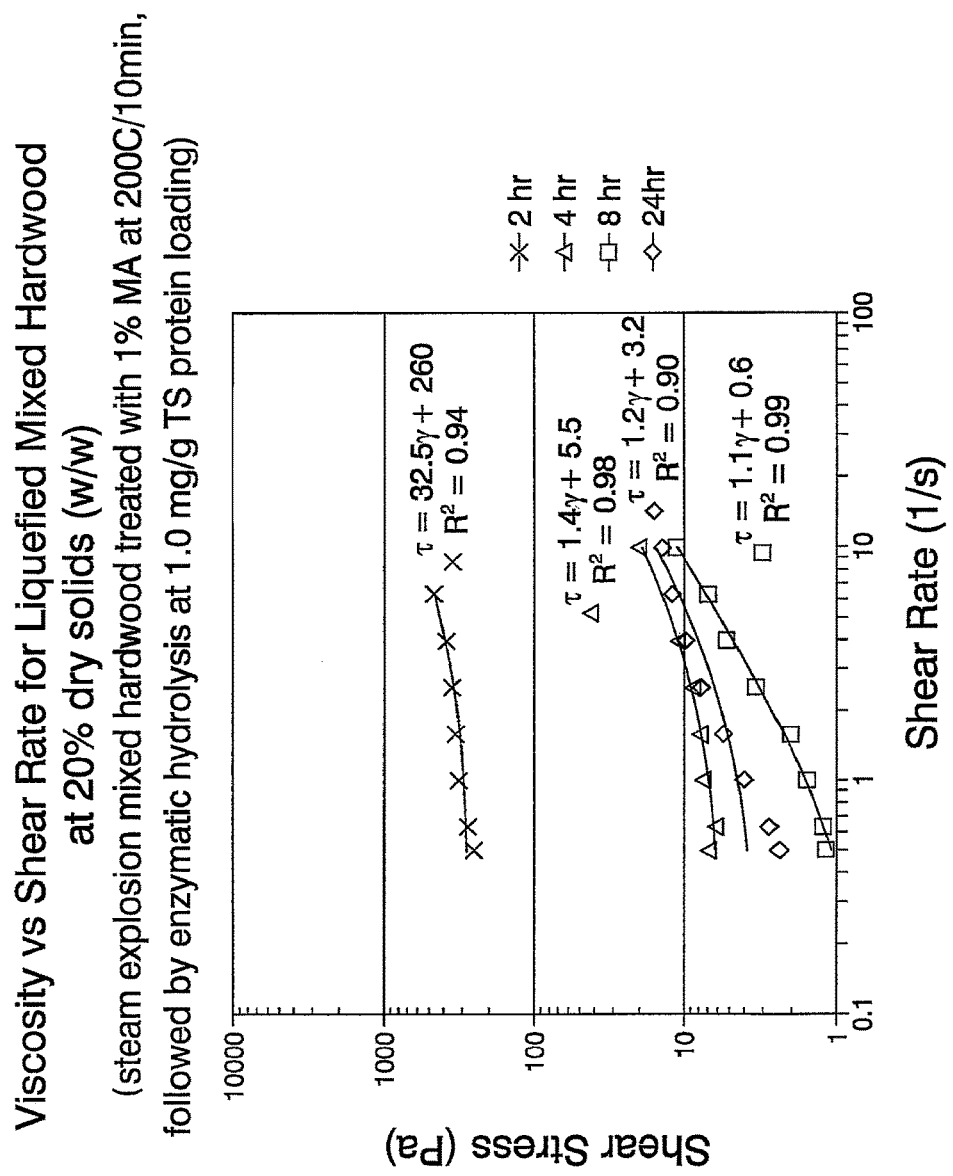
FIG. 13 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 1 mg protein per gram of total dry solids biomass charged to the process, as described further in Example 4.
Figure 14:
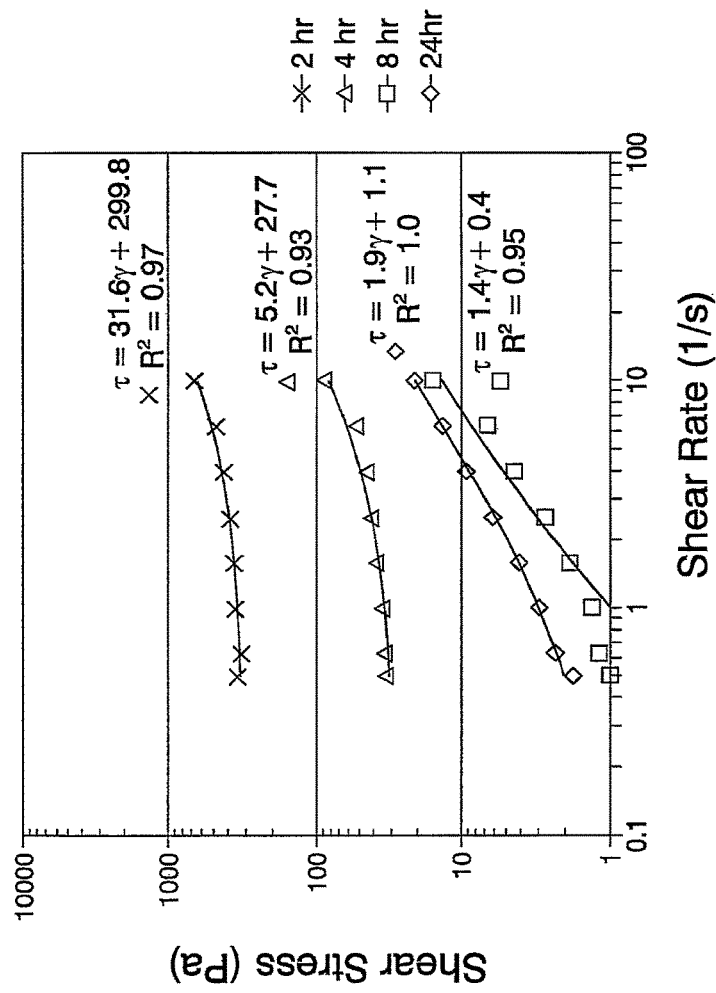
FIG. 14 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 0.5 mg protein per gram of total dry solids biomass charged to the process, as described further in Example 4.
Figure 15:
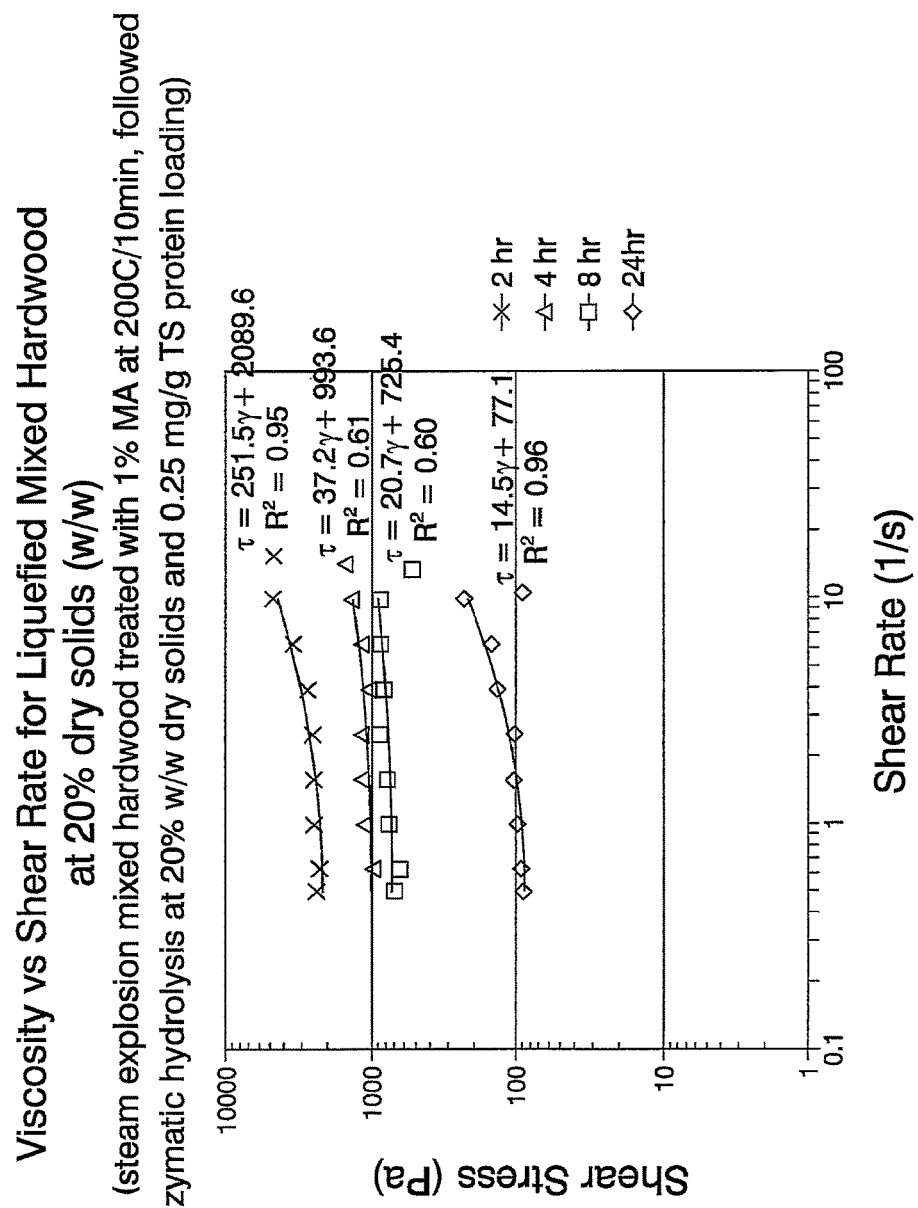
FIG. 15 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 0.25 mg protein per gram of total dry solids biomass charged to the process, as described further in Example 4.
Figure 16:
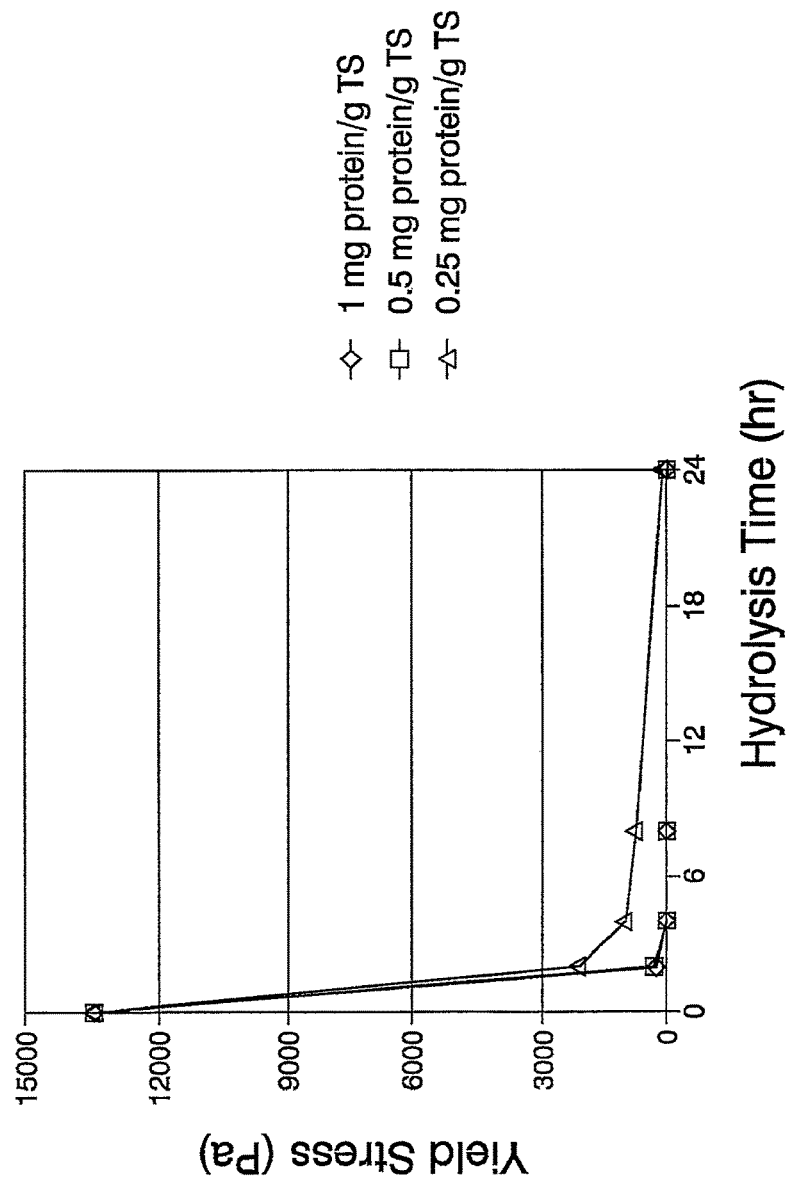
FIG. 16 provides a graph of yield stress (Pa) versus enzyme hydrolysis time for liquefied compositions from dual-step digestions including treatment of 20% dry solids of previously steam-exploded, mixed hardwood with 1% maleic acid at 200° C. followed by neutralization and cellulase digestion for 2, 4, 8 or 24 hours with 1, 0.5, and 0.25 mg protein per gram of total dry solids biomass charged to the process, as described further in Example 4.
Figure 17:
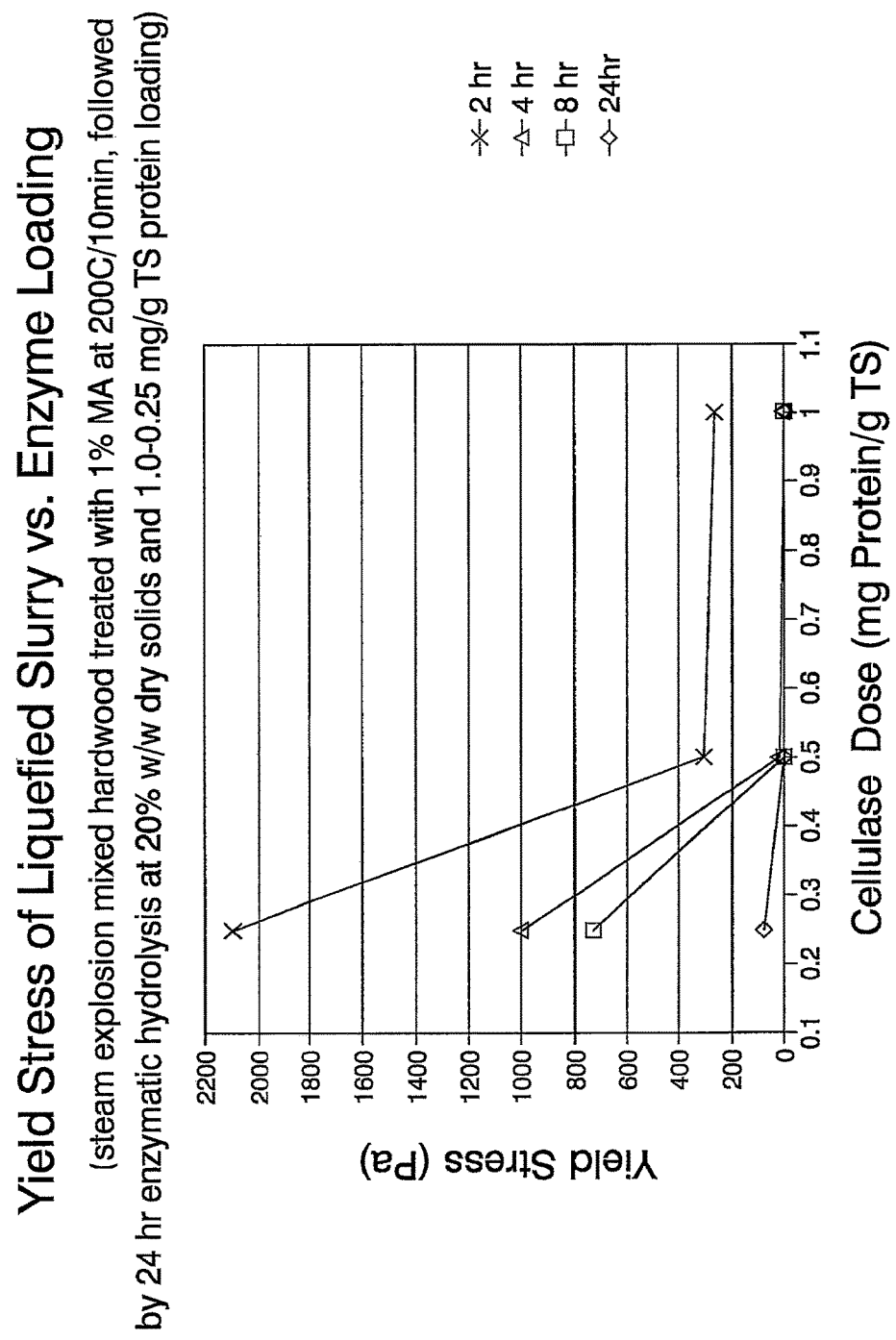
FIG. 17 provides a graph of yield stress (Pa) versus cellulase dose for liquefied compositions from the dual-step digestions also plotted in FIG. 16 and described in Example 4.

The results are presented graphically in FIGS. 13-17, which demonstrate that enzyme loadings and incubation times can be selected to significantly improve the flow properties of the biomass digest. FIGS. 13-15 plot shear stress (PA) versus shear rate (1/S) for the processed samples, and demonstrate that at enzyme loadings of 1 mg and 0.5 mg of protein per gram of biomass solids (FIGS. 13 and 14, respectively), the ratio of shear stress to shear rate remained relatively high for 2-hour enzyme incubation runs, whereas 4-hour, 8-hour and 24-hour enzyme incubation runs resulted in a comparatively much lower ratio of shear stress to shear rate. As shown in FIG. 15, significant improvements in flow properties of the biomass digest can be achieved even when using a very low enzyme loading of 0.25 mg protein per gram of total biomass solids, with longer incubation times providing a decreasing ratio of shear stress to shear rate in the studies. FIG. 16 plots the yield stress of the digest samples versus hydrolysis time for varied enzyme loadings, and FIG. 17 plots the yield stress of digest samples versus enzyme loading for various hydrolysis times. As shown, the yield stress of the digested biomass materials was very substantially decreased at all enzyme loadings, even after a relatively short (2 hour) enzyme incubation period. Generally, longer incubation periods and/or enzyme loadings can be selected to result in lower yield stress digest materials.

Example 5

Rheologic Properties of Liquefied Biomass

Figure 18:
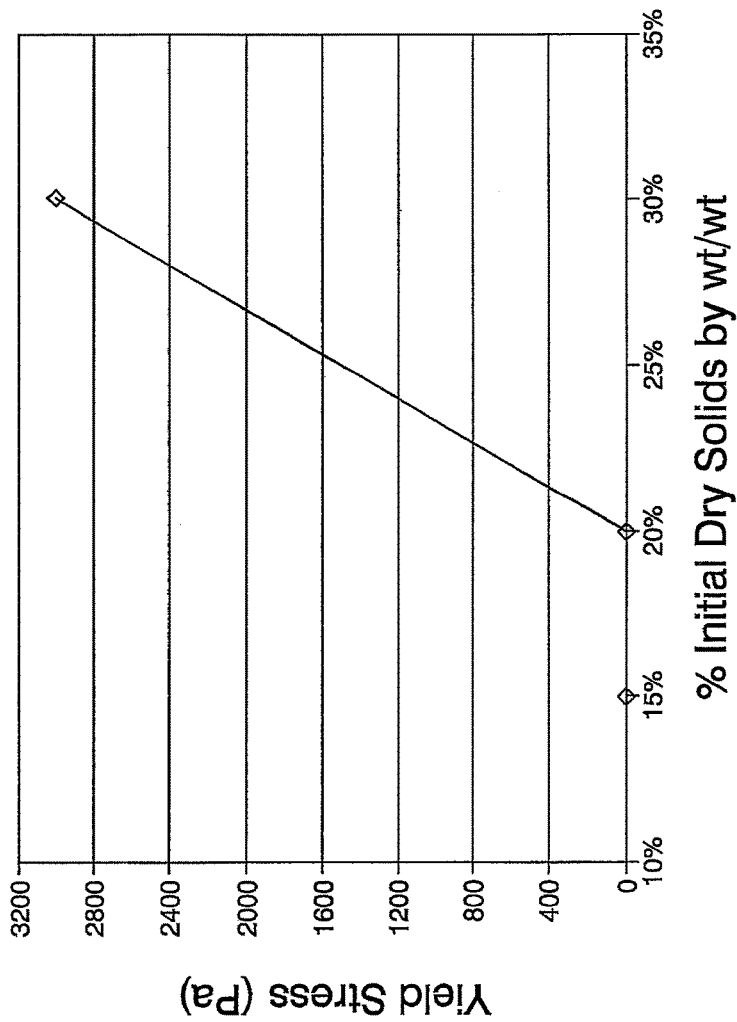
FIG. 18 provides a graph of yield stress (Pa) versus percent initial dry solids (wt/wt) for liquefied compositions from dual-step digestions including treatment of 15%, 20% and 30% dry solids of previously steam-exploded, mixed hardwood with 1% maleic acid at 200° C. followed by neutralization and cellulase digestion for 8 hours with 1 mg protein per gram of total dry solids biomass charged to the process, as described further in Example 5.
Figure 19:
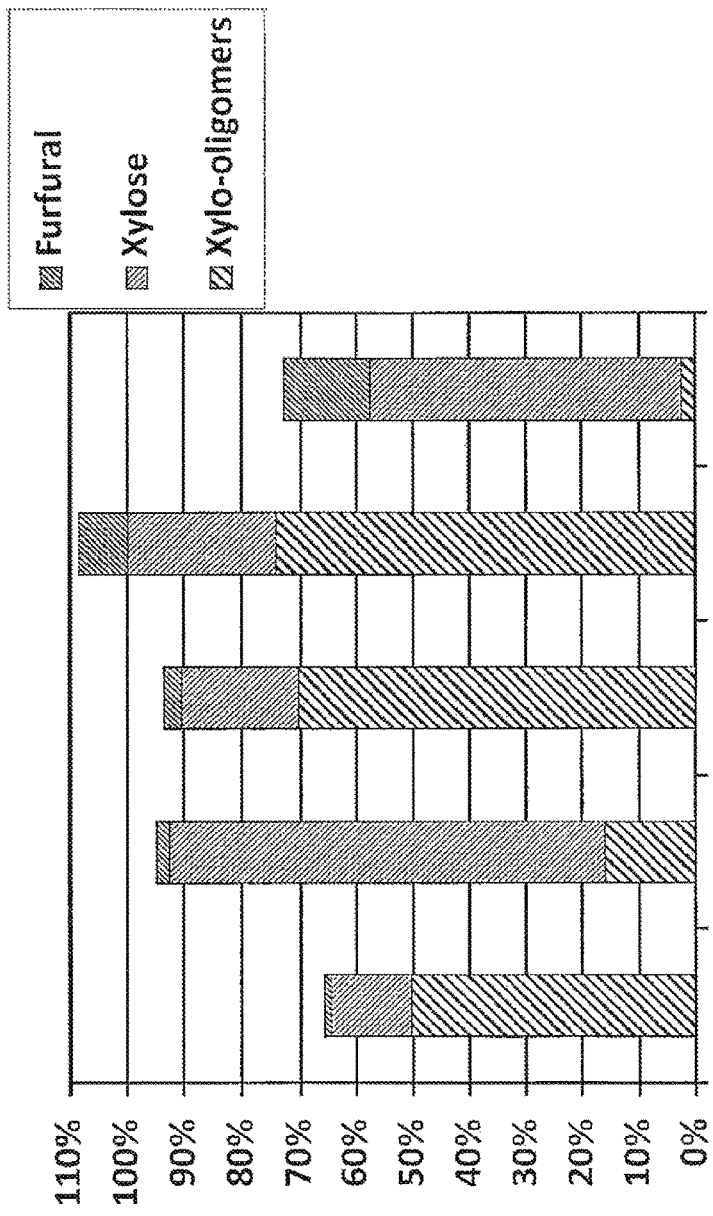
FIG. 19 provides a graph of xylose and xylo-oligomer concentration in digest slurries prepared as in Example 6.

This example demonstrates that digest compositions of mixed hardwood resultant of sequential dicarboxylic acid (maleic acid) and enzyme hydrolysis exhibit advantageous rheologic properties for downstream unit operations over varied dry solids loadings at the start of the process. Samples of steam-exploded, mixed hardwood were subjected to sequential maleic acid and enzyme hydrolysis as described in Example 5, except using 15%, 20% and 30% by weight biomass solids, and using an enzyme digestion period of 8 hours. The entire resulting biomass digest composition was tested for rheologic properties with a Rheometer ARG2 (TA Instruments, Inc.) and yield stresses for the samples were calculated as in Example 4. The results, shown in FIG. 18, demonstrate that under the conditions employed, increasing starting biomass solids loadings above 20% led to increasing yield stress values for the digest compositions. It will be understood that higher dicarboxylic acid (maleic acid) concentrations and/or longer incubation periods, for example, could be used to result in lower yield stress values for high-solids starting materials.

Example 6

Low-Temperature Mimetic Liquefaction

This example demonstrates that beneficial digest compositions of mixed hardwood can be prepared using low-temperature dicarboxylic acid (maleic acid) hydrolysis in which very highly-selective, enzyme-like activity is exhibited. Samples of steam-exploded, mixed hardwood were subjected to maleic acid hydrolysis at varied relatively low temperatures as follows.

Figure 20:
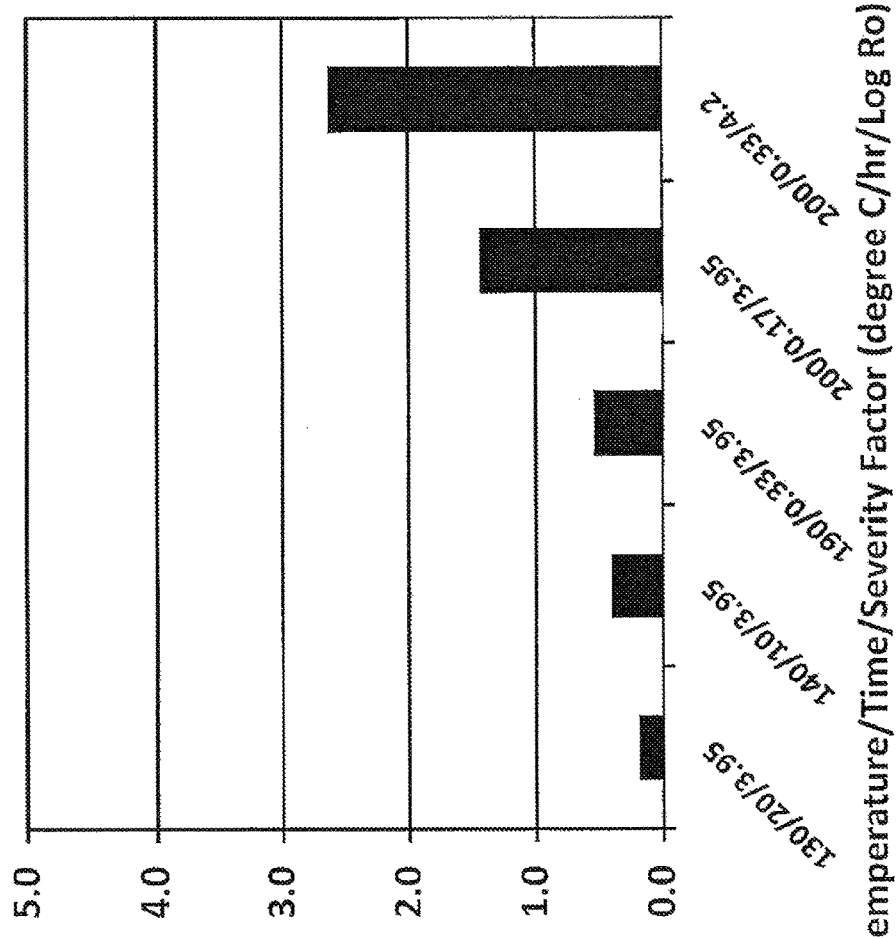
FIG. 20 provides a graph of furfural concentrations plotted in FIG. 19 and described in Example 6.
Figure 21:
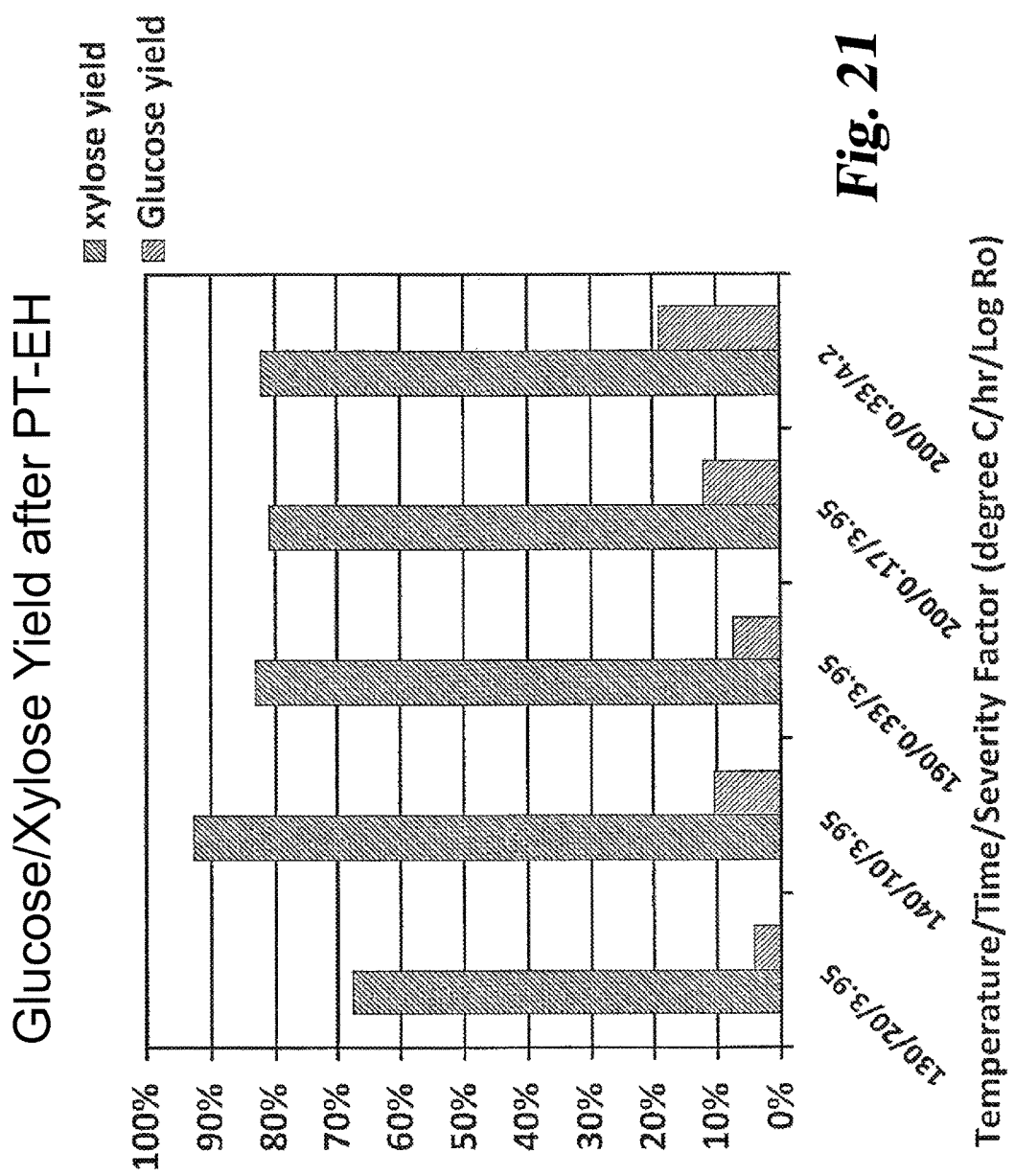
FIG. 21 provides a graph of monomeric glucose yields from dual-step digestions including treatment of 15% dry solids of mixed hardwood with 0.5% maleic acid under varied temperature/time conditions followed by neutralization and 24-hour cellulase digestions with 1 mg protein per gram of total dry solids of biomass charged to the process, as described further in Example 6.
Figure 22:
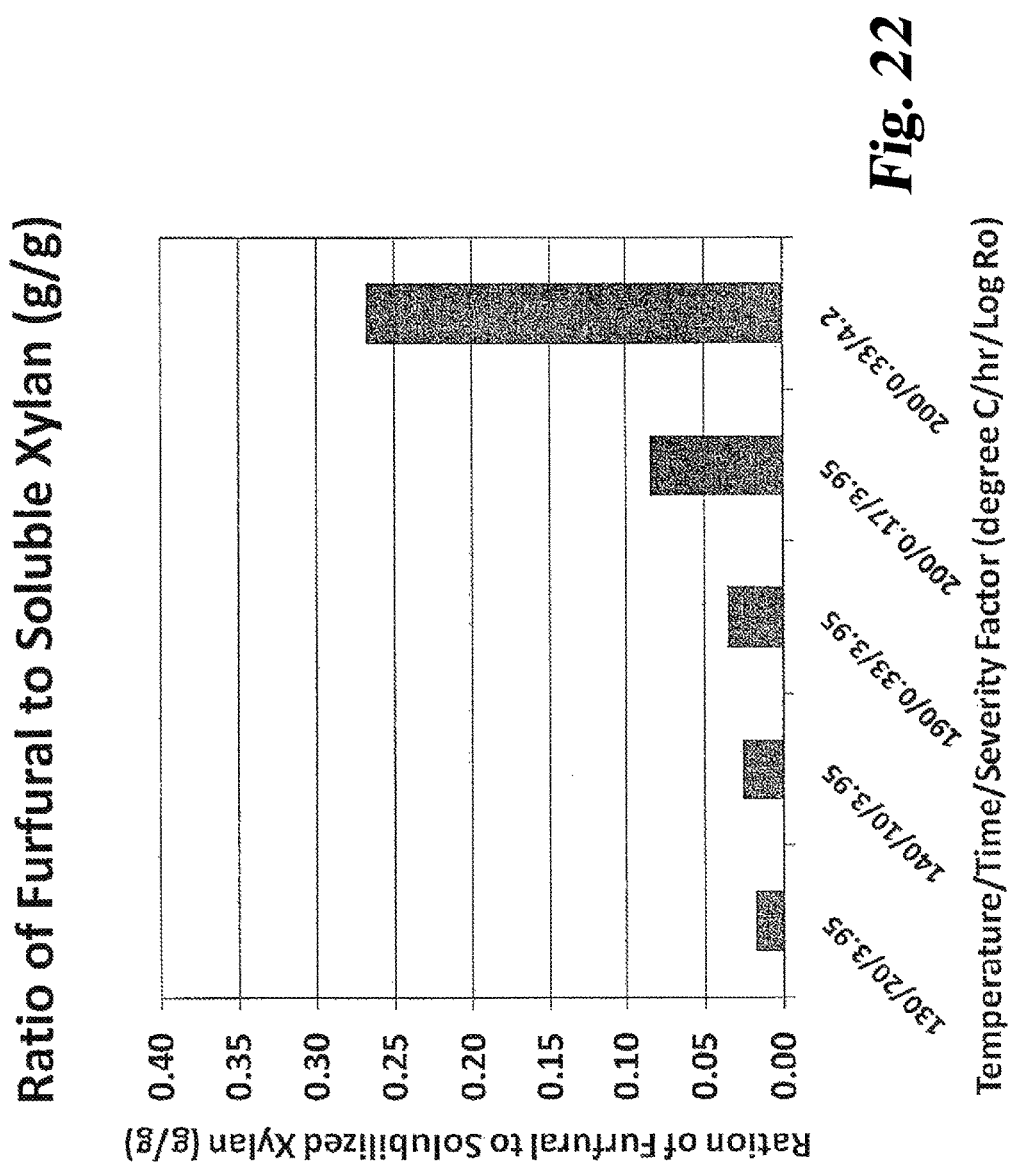
FIG. 22 provides a graph of ratio of furfural to solubilized xylan from digestions including treatment of 15% dry solids of mixed hardwood with 0.5% maleic acid under varied temperature/time conditions, as described further in Example 6.

Samples (50-100 g each) of the mixed hardwood pin chips (average particle length about 0.5-1.0 inch) were soaked in the maleic acid solution overnight at solids loadings of 15%. The next day, in a sealed reaction vessel, the slurry was preheated to 140° C. for 10 minutes (essentially no reaction occurring) and then moved to a sandbath heated to the target temperature (Table 2). The samples were then given a period of 5 minutes to reach the target temperature and then kept in the sandbath for an additional period as shown in Table 2. The resulting digests as a whole were neutralized with ammonium hydroxide and charged respectively to a 250 mL Nalgene plastic bottle with cellulase enzyme (Spezyme CP (Genencor, A Danisco Division); Novozyme 188 (Novozyme); Multifect Pectinase (Genencor, A Danisco Division)) at 1 mg enzyme per gram of total starting biomass solids (dry weight). Enzyme hydrolysis was conducted for 24 hours at 50° C., pH 4.8, with stirring at 200 rpm, with samples taken at various intervals to measure glucose, gluco-oligomer, xylose, xylo-oligomer and furfural concentrations. The results are shown in FIG. 19-22 and demonstrated significant liquefaction and saccharification of the biomass by the dicarboxylic acid mimetic with high selectivity for fermentable sugar. The selectivity for soluble xylose and xylo-oligomers ("soluble xylan") versus furfural in the mimetic-pretreated digest was surprisingly good at longer times and lower temperatures while also providing good sugar yields (see FIGS. 19 and 22). Correspondingly, the furfural concentration in the mimetic-pretreated digest was higher in the samples treated at higher temperatures and for shorter times (FIG. 20). The xylose and glucose yields after mimetic pretreatment and subsequent enzymatic hydrolysis (PT-EH) are shown in FIG. 21, with good yields being obtainable even in relatively low temperature runs.

TABLE 2

Severity defined as a function of times and temperatures

| Temperature (° C.) | Time (hr) | severity factor (Log $R_o$) |
|---|---|---|
| 130 | 20 | 3.95 |
| 140 | 10 | 3.95 |
| 190 | 0.33 | 3.95 |
| 200 | 0.17 | 3.95 |
| 200 | 0.33 | 4.2 |

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

The invention claimed is:

1. A method for processing lignocellulosic biomass, comprising:

providing a solid, particulate biomass, wherein said solid, particulate biomass is grass, sugar cane bagasse, sugar beet pulp, soybean stover, corn fiber, corn stover, oat straw, rice straw, rice hulls, barley straw, corn cobs, wheat straw, canola straw, oat hulls, wood, paper sludge, newsprint, or cardboard;

incubating a mixture comprising a first amount of said solid, particulate lignocellulosic biomass and a first amount of a liquid processing medium containing at least one dicarboxylic acid under heated conditions effective to form from the mixture a biomass digest composition exhibiting a yield stress that is less than half that of the mixture, said yield stress of the biomass digest composition being less than 15000 Pascals, and in which at least 10% by weight of the solid, particulate biomass has been converted to dissolved biomass components in the liquid medium including monomeric xylose and xylose oligomers, the digest composition also including undissolved lignocellulosic biomass particulates formed from the solid, particulate biomass, said undissolved lignocellulosic biomass particulates including lignin and cellulose;

pumping a lignocellulosic particulate digest slurry at least partially comprised of said dissolved biomass components including the monomeric xylose and xylose oligomers and at least partially comprised of said undissolved lignocellulosic biomass particulates through a first passage of a heat exchanger while passing a second amount of a liquid processing medium containing at least one dicarboxylic acid through a second passage of the heat exchanger so as to transfer heat from said lignocellulosic particulate digest slurry to said second amount of liquid processing medium to provide a preheated liquid processing medium; and combining the preheated liquid processing medium with a second amount of said solid, particulate biomass.

2. The method of claim 1, wherein the heat exchanger is a spiral heat exchanger.

3. The method of claim 1, wherein the heat exchanger is a plate heat exchanger.

4. The method of claim 1, wherein the biomass digest composition exhibits a yield stress in the range of 10000 Pascals to less than 15000 Pascals.

5. The method of claim 1, wherein said pumping is at a flow rate of at least about 20 gallons per minute.

6. The method of claim 1, wherein the digest composition comprises at least about 20 g/L of monomeric xylose.

7. The method of claim 1, wherein the digest composition is constituted at least about 55% of undissolved solids.

8. The method of claim 1, also comprising hydrolyzing the undissolved, lignocellulosic biomass particulates from the digest composition with cellulase to convert cellulose in the biomass particulate to glucose.

9. The method of claim 8, wherein said hydrolyzing is conducted after said pumping.

10. The method of claim 1, also comprising neutralizing said digest composition with a base.

11. The method of claim 1, wherein said pumping comprises pumping with a centrifugal pump.

12. The method of claim 1, wherein said pumping is sufficient to cause flow of the lignocellulosic particulate digest slurry through said first passage at a linear velocity of at least about 1 foot per second.

13. The method of claim 1, wherein the first amount of the solid, particulate lignocellulosic biomass, on a dry weight basis, constitutes at least 15% by weight of the mixture.

14. The method of claim 1, wherein the liquid processing medium of the mixture is at least 80% aqueous.

15. The method of claim 1, also comprising, after said pumping and before said combining, flashing liquid from the lignocellulosic particulate digest slurry to vapors, and condensing the vapors upon and thereby heating the second amount of said solid, particulate lignocellulosic biomass.

16. The method of claim 1, wherein the biomass digest composition is comprised at least 15% by weight total biomass solids on a dry weight basis, and wherein 10% to 45% of the total biomass solids are dissolved in the liquid medium.

17. The method of claim 1, wherein the first passage has an inlet and an outlet, and wherein during said pumping the slurry experiences a pressure drop of no greater than about 20 psi.

18. The method of claim 1, wherein said incubating comprises incubating the mixture in a vessel.

19. The method of claim 18, wherein said incubating comprises heating the mixture with steam injected into the vessel.

20. The method of claim 18, wherein for at least a portion of a duration of said incubating, the mixture is not subjected to mechanical mixing.

21. The method of claim 1, wherein the lignocellulosic particulate digest slurry is comprised at least 10% by weight, on a dry weight basis, of particles having a maximum dimension greater than about 1 cm.

22. The method of claim 2, wherein the spiral heat exchanger has a gap width of about 1 to 4 cm.

23. The method of claim 7, wherein the lignocellulosic particulate digest slurry includes the digest composition.

24. The method of claim 23, wherein the digest composition is undiluted in the lignocellulosic particulate digest slurry.

25. The method of claim 23, wherein the digest composition is diluted in the lignocellulosic particulate digest slurry.

26. The method of claim 25, wherein during said pumping, the digest slurry passes through the first passage at a linear velocity in the range of about 10 to about 50 feet per second.

27. A method for processing lignocellulosic biomass, comprising:

providing a solid, particulate biomass, wherein said solid, particulate biomass is grass, sugar cane bagasse, sugar beet pulp, soybean stover, corn fiber, corn stover, oat straw, rice straw, rice hulls, barley straw, corn cobs, wheat straw, canola straw, oat hulls, wood, paper sludge, newsprint, or cardboard;

subjecting said solid, particulate lignocellulosic biomass to acid-catalyzed liquefaction by incubating a mixture containing said solid, particulate biomass and at least one dicarboxylic acid under heated conditions effective to form from the mixture a biomass digest slurry exhibiting a yield stress that is less than half that of the mixture, said yield stress of the biomass digest slurry being less than 15000 Pascals, and in which at least 10% by weight of the solid, particulate biomass has been converted to dissolved biomass components in the liquid medium including monomeric xylose and xylose oligomers, the digest slurry also including undissolved, finely-divided lignocellulosic biomass particulates formed from the solid, particulate biomass, wherein the finely-divided lignocellulosic biomass particulates flow freely with the liquid medium; and pumping a lignocellulosic particulate digest slurry including the dissolved biomass components including the monomeric xylose and the xylose oligomers and the undissolved, finely-divided lignocellulosic biomass particulates through a first passage of a heat exchanger while passing a liquid medium through a second passage of the heat exchanger so as to transfer heat from the lignocellulosic particulate digest slurry to the liquid medium.

28. The method of claim 27, wherein the lignocellulosic biomass comprises wood.

29. The method of claim 27, wherein the heat exchanger is a spiral heat exchanger.

30. The method of claim 27, also comprising:
after said pumping, contacting the particulate lignocellulosic biomass slurry with a cellulolytic enzyme so as to hydrolyze amounts of cellulose to form glucose.

31. The method of claim 27, wherein said pumping comprises pumping with a centrifugal pump.

32. The method of claim 31, wherein said pumping is sufficient to cause flow of the slurry through said first passage at a linear velocity of at least about 1 foot per second.

33. The method of claim 27, wherein said first amount of the solid, particulate lignocellulosic biomass, on a dry weight basis, constitutes at least 15% by weight of the mixture.

34. The method of claim 33, wherein the liquid processing medium of said mixture is at least about 80% aqueous.

* * * * *